(12) United States Patent
Pulé et al.

(10) Patent No.: US 11,492,408 B2
(45) Date of Patent: *Nov. 8, 2022

(54) BI-SPECIFIC T-CELL ENGAGER SPECIFIC FOR BCMA

(71) Applicant: UCL BUSINESS LTD, London (GB)

(72) Inventors: Martin Pulé, London (GB); Kwee Yong, London (GB); Lydia Lee, London (GB); Neil Chaplin, London (GB)

(73) Assignee: UCL BUSINESS LTD, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/028,113

(22) PCT Filed: Oct. 10, 2014

(86) PCT No.: PCT/GB2014/053056
§ 371 (c)(1),
(2) Date: Apr. 8, 2016

(87) PCT Pub. No.: WO2015/052536
PCT Pub. Date: Apr. 16, 2015

(65) Prior Publication Data
US 2016/0311915 A1    Oct. 27, 2016

(30) Foreign Application Priority Data
Oct. 10, 2013    (GB) .................................... 1317928

(51) Int. Cl.
*C07K 16/28*    (2006.01)

(52) U.S. Cl.
CPC ...... *C07K 16/2878* (2013.01); *C07K 16/2809* (2013.01); *C07K 2317/31* (2013.01); *C07K 2317/53* (2013.01); *C07K 2317/565* (2013.01); *C07K 2317/622* (2013.01); *C07K 2319/33* (2013.01); *C07K 2319/74* (2013.01)

(58) Field of Classification Search
CPC ............ C07K 16/2878; C07K 16/2809; C07K 2317/565; C07K 2317/622; C07K 2317/31
USPC .......................................... 424/133.1, 136.1
See application file for complete search history.

(56) References Cited

U.S. PATENT DOCUMENTS

| | | | | |
|---|---|---|---|---|
| 10,072,088 | B2* | 9/2018 | Pillarisetti | C07K 16/2809 |
| 10,160,794 | B2* | 12/2018 | Pule | C12N 15/85 |
| 10,172,885 | B2* | 1/2019 | Pule | A61K 39/0011 |
| 10,172,886 | B2* | 1/2019 | Pule | A61K 39/0011 |
| 10,611,811 | B2* | 4/2020 | Pule | C12N 15/85 |
| 10,752,665 | B2* | 8/2020 | Pule | A61P 35/02 |
| 2014/0370013 | A1* | 12/2014 | Desjarlais | C07K 16/2809 |
| | | | | 424/135.1 |
| 2015/0368351 | A1* | 12/2015 | Vu | C07K 16/2878 |
| | | | | 424/136.1 |
| 2015/0376287 | A1* | 12/2015 | Vu | C07K 16/2878 |
| | | | | 424/136.1 |
| 2016/0237139 | A1* | 8/2016 | Pule | A61K 35/17 |
| 2016/0289293 | A1* | 10/2016 | Pule | A61K 39/0011 |
| 2016/0289294 | A1* | 10/2016 | Pule | A61K 39/0011 |
| 2016/0296562 | A1* | 10/2016 | Pule | A61K 39/0011 |
| 2016/0362467 | A1* | 12/2016 | Pule | C07K 14/525 |
| 2017/0037131 | A1* | 2/2017 | Bernett | C07K 16/2812 |
| 2017/0218077 | A1* | 8/2017 | Raum | C07K 16/2866 |
| 2017/0306036 | A1* | 10/2017 | Vu | A61P 35/00 |
| 2017/0334964 | A1* | 11/2017 | Pule | C07K 14/525 |
| 2019/0038672 | A1* | 2/2019 | Pule | A61K 39/0011 |
| 2019/0100571 | A1* | 4/2019 | Pule | C07K 14/70575 |
| 2021/0355217 | A1* | 11/2021 | Pulé | C07K 16/2809 |
| 2022/0033509 | A1* | 2/2022 | Pulé | A61K 35/17 |
| 2022/0041718 | A1* | 2/2022 | Bulek | C07K 14/70517 |

FOREIGN PATENT DOCUMENTS

| | | |
|---|---|---|
| CN | 102219856 A | 10/2011 |
| CN | 102372778 A | 3/2012 |
| CN | 102574921 A | 7/2012 |
| JP | H06315383 A | 11/1994 |
| JP | 2000502562 A | 3/2000 |
| JP | 2007181458 A | 7/2007 |
| JP | 2007532480 A | 11/2007 |
| JP | 2009539413 A | 11/2009 |
| JP | 2012504970 A | 3/2012 |
| JP | 2013513370 A | 4/2013 |
| WO | WO-9723613 A2 | 7/1997 |
| WO | WO-2004027026 A2 | 4/2004 |
| WO | WO-201042904 A2 | 4/2010 |
| WO | WO-201 1/039126 A1 | 4/2011 |
| WO | WO-2012/066058 A1 | 5/2012 |
| WO | WO-2012130471 A1 | 10/2012 |

(Continued)

OTHER PUBLICATIONS

Kane et al. Current Opinion in Immunology 2000, 12:242-249.*
Hipp et al. (Leukemia (2017) 31, 1743-1751).*
Hymowitz et al., Structures of APRIL-receptor complexes: like BCMA, TACI employs only a single cysteine-rich domain for high affinity ligand binding, J. Biol. Chem., 280(8):7218-27 (2005).
Lee et al., Evaluation of B cell maturation antigen as a target for antibody drug conjugate mediated cytotoxicity in multiple myeloma, Br. J. Haematol., 174(6):911-22 (2016).
Search Report, United Kingdom patent application No. GB1317928.8, dated Jun. 27, 2014.
Yang et al., APRIL promotes survival and proliferation of T cells: Imiplications for T-cell lymphoma, Blood, vol. 104, No. 11, part 1, p. 725A (2004).

(Continued)

*Primary Examiner* — Lynn A Bristol
(74) *Attorney, Agent, or Firm* — Marshall, Gerstein & Borun LLP

(57) ABSTRACT

The present invention provides a bi-specific molecule which comprises: (i) a first domain which binds B cell maturation antigen (BCMA) and comprises at least part of a proliferation-inducing ligand (APRIL); and (ii) a second domain capable of activating a T cell. The invention also provides the use of such a molecule in the treatment of plasma-cell mediated diseases, such as multiple myeloma.

11 Claims, 10 Drawing Sheets

Specification includes a Sequence Listing.

(56) References Cited

FOREIGN PATENT DOCUMENTS

| WO | WO-2013/072406 A1 | 5/2013 |
| WO | WO-2013/072415 A1 | 5/2013 |

OTHER PUBLICATIONS

Kolfschoten et al., TWE-PRIL; a fusion protein of TWEAK and APRIL, Biochem. Pharmacol., 66(8):1427-32 (2003).

International Search Report and Written Opinion, International Application No. PCT/GB2014/053056, dated Mar. 6, 2015.

Kimberley et al., The proteoglycan (heparan sulfate proteoglycan) binding domain of APRIL serves as a platform for ligand multimerization and cross-linking, Shinkei Kagaku—Bulletin of the Japanese Neurochemical Society, 23(5):1584-95 (2009).

Lee et al., Designing APRIL-based therapeutics for targeting BCMA in multiple myeloma, American Society of Gene and Cell Therapy 17th Annual Meeting: Simultaneous Oral Abstract Sessions in Cancer-Targeted Gene & Cell Therapy (May 22, 2014).

Lee et al., Designing APRIL-based therapeutics for targeting BCMA in multiple myeloma, UK Myeloma Forum ASH 2013 Winning Abstracts (uploaded document created on Oct. 25, 2013).

SA1312149, Sequence of APRIL (Seq ID No. 2), Retrieved from the Internet at: <htttp.ibis.internal.epo.org/exam/jobResult?id=299566>, on Jan. 5, 2015.

Kimberley et al., The proteoglycan (heparan sulfate proteoglycan) binding domain of APRIL serves as a platform for ligand multimerization and cross-linking, FASEB J., 23(5):1584-95 (2009).

Khattar et al., B-Cell Maturation Antigen is exclusively expressed in a wide range of B-Cell and Plasma Cell Neoplasm and in a potential therapeutic target for Bcma directed therapies, Blood, 2017, vol. 130, suppl. 1, p. 2755.

Search ReportforJP Application No. 2016-521332 dated Jul. 13, 2018.

Notice of Reasons for Refusal for JP Application No. 2016-521332 dated Aug. 2, 2018.

Decision to Grant for JP Application No. 2016-521332 dated Jul. 2, 2019.

Matsushita T et al., The Role of BAFF in Autoimmune Diseases, Japan Society for Clinical Immunology, 2005, vol. No. 28(5) pp. 333-342.

De Bruyn M et al., Cell Surface Delivery of Trail Strongly Augments the Tumoricidal Activity of Tcells, Clin Cancer Research, Jul. 13, 2011, vol. 17(17) pp. 5626-5637.

* cited by examiner

METDTLLLWVLLLWVPGSTGQVQLQQSGAELARPGASVKMSCKASGYTFTRYTMHWVKQRPGQGLEWIGYINPSRGYTNYNQKFKDKATL
TTDKSSSTAYMQLSSLTSEDSAVYYCARYYDDHYCLDYWGQGTTLTVSSSGGGGSGGGGSGGGGSQIVLTQSPAIMSASPGEKVTMTCSA
SSSVSYMNWYQQKSGTSPKRWIYDTSKLASGVPAHFRGSGSGTSYSLTISGMEAEDAATYYCQQWSSNPFTFGSGTKLEINRSDPAEPK
SDKTHTCPPCPKDPFSGGGGSVLHLVPINATSKDDSDVTEVMWQPALRRGRGLQAQGYGVRIQDAGVYLLYSQVLFQDVTFTMGQVVSRE
GQGRQETLFRCIRSMPSHPDRAYNSCYSAGVFHLHQGDILSVIIPRARAKLNLSPHGTFLGFVKL

| | |
|---|---|
| Signal peptide | Compact highly efficient signal peptide with predicted ~95% cleavage after the terminal glycine. |
| OKT3 scFv | Single-chain variable fragment from OKT3. The heavy and light chain variable regions have been isolated from native signal peptide and constant regions and linked together with a SGGGGS3 linker. |
| SDP linker | This is another linker motif we use to introduce a chain-break (separate two distinct domains but allows orientation in different angles). Also conveniently codes for a BamHI restriction site |
| IgG1 hinge | The human IgG1 hinge sequence. |
| SGGGGS linker | Serine-glycine linker to connect the carboxy-terminus onto truncated APRIL. |
| dAPRIL | APRIL truncated as discussed above after Ingold[1] |

FIG. 8a

METDTLLLWVLLLWVPGSTGQVQLQQSGAELARPGASVKMSCKASGYTFTRYTMHWVKQRPGQGLEWIGYINPSRGYTNYNQKFKDKATL
TTDKSSSTAYMQLSSLTSEDSAVYYCARYYDDHYCLDYWGQGTTLTVSSSGGGGSGGGGSGGGGSQIVLTQSPAIMSASPGEKVTMTCSA
SSSVSYMNWYQQKSGTSPKRWIYDTSKLASGVPAHFRGSGSGTSYSLTISGMEAEDAATYYCQQWSSNPFTFGSGTKLEINRSDPTTPA
PRPPTPAPTIASQPLSLRPEACRPAAGGAVHTRGLDFACDSGGGGSVLHLVPINATSKDDSDVTEVMWQPALRRGRGLQAQGYGVRIQDA
GVYLLYSQVLFQDVTFTMGQVVSREGQGRQETLFRCIRSMPSHPDRAYNSCYSAGVFHLHQGDILSVIIPRARAKLNLSPHGTFLGFVKL

| | |
|---|---|
| Signal peptide | Signal peptide as per APRILiTE#03 |
| OKT3 scFv | Single-chain variable fragment from OKT3 in heavy light orientation |
| SDP linker | Linker motif we use to introduce a chain-break. Also conveniently codes for a BamHI restriction site |
| CD8α stalk | The stalk structure for CD8α |
| SGGGGS linker | Serine-glycine linker to connect the carboxy-terminus onto truncated APRIL. |
| dAPRIL | APRIL truncated as discussed above. |

FIG. 8b

MGTSLLCWMALCLLGADHADGVLHLVPINATSKDDSDVTEVMWQPALRRGRGLQAQGYGVRIQDAGVYLLYSQVLFQDVTFTMGQVVSRE
GQGRQETLFRCIRSMPSHPDRAYNSCYSAGVFHLHQGDILSVIIPRARAKLNLSPHGTFLGFVKL*SGGGSDP*TTTPAPRPPTPAPTIASQ
PLSLRPEACRPAAGGAVHTRGLDFACDSGGGGSSQVQLQQSGAELARPGASVKMSCKASGYTFTRYTMHWVKQRPGQGLEWIGYINPSRGY
TNYNQKFKDKATLTTDKSSSTAYMQLSSLTSEDSAVYYCARYYDDHYCLDYWGQGTTLTVSSSGGGGSGGGGSGGGGSQIVLTQSPAIMS
ASPGEKVTMTCSASSSVSYMNWYQQKSGTSPKRWIYDTSKLASGVPAHFRGSGSGTSYSLTISGMEAEDAATYYCQQWSSNPFTFGSGTK
LEINRS

| Signal peptide | Compact highly efficient signal peptide with predicted ~95% cleavage after the terminal glycine. A highly efficient signal peptide is needed to |
| --- | --- |
| dAPRIL | APRIL truncated |
| SGGGSDP | Flexible linker and chain break |
| CD8α stalk | The stalk structure for CD8α |
| Linker | Serine-glycine linker to connect the carboxy-terminus onto truncated APRIL. |
| OKT3 scFv | Single-chain variable fragment from OKT3 |

FIG. 8c

BI-SPECIFIC T-CELL ENGAGER SPECIFIC FOR BCMA

SEQUENCE LISTING

This application contains, as a separate part of the disclosure, a sequence listing in computer-readable form (50599_SeqListing.txt; 26,875 bytes; created Apr. 7, 2016), which is incorporated by reference in its entirety.

FIELD OF THE INVENTION

The present invention relates to a bispecific molecule which binds the B cell maturation antigen (BCMA) and activates T-cells. The molecule is useful in the treatment of plasma cell diseases such as multiple myeloma.

BACKGROUND TO THE INVENTION

Multiple Myeloma

Multiple Myeloma (myeloma) is a bone-marrow malignancy of plasma cells. Collections of abnormal plasma cells accumulate in the bone marrow, where they interfere with the production of normal blood cells. Myeloma is the second most common hematological malignancy in the U.S. (after non-Hodgkin lymphoma), and constitutes 13% of haematologic malignancies and 1% of all cancers. The disease is burdensome in terms of suffering as well as medical expenditure since it causes pathological fractures, susceptibility to infection, renal and then bone-marrow failure before death.

Unlike many lymphomas, myeloma is currently incurable. Standard chemotherapy agents used in lymphoma are largely ineffective for myeloma. In addition, since CD20 expression is lost in plasma cells, Rituximab cannot be used against this disease. New agents such as Bortezamib and Lenolidomide are partially effective, but fail to lead to long-lasting remissions.

There is thus a need for alternative agents for the treatment of myeloma which have increased efficacy and improved long-term effects.

Bispecific Antibodies

A wide variety of molecules have been developed which are based on the basic concept of having two antibody-like binding domains.

Bispecific T-cell engaging molecules are a class of bispecific antibody-type molecules that have been developed, primarily for the use as anti-cancer drugs. They direct a host's immune system, more specifically the T cells' cytotoxic activity, against a target cell, such as a cancer cell. In these molecules, one binding domain binds to binds to a T cell via the CD3 receptor, and the other to a target cells such as a tumor cell (via a tumor specific molecule). Since the bispecific molecule binds both the target cell and the T cell, it brings the target cell into proximity with the T cell, so that the T cell can exert its effect, for example, a cytotoxic effect on a cancer cell. The formation of the T cell:bispecific Ab:cancer cell complex induces signaling in the T cell leading to, for example, the release of cytotoxic mediators. Ideally, the agent only induces the desired signaling in the presence of the target cell, leading to selective killing.

Bispecific T-cell engaging molecules have been developed in a number of different formats, but one of the most common is a fusion consisting of two single-chain variable fragments (scFvs) of different antibodies. These are sometimes known as BiTEs (Bi-specific T-cell Engagers).

WO2012/066058 and WO2013/072415 both describe BiTEs which comprise an scFv which binds the B-cell maturation antigen (BCMA).

BCMA is a transmembrane protein that is preferentially expressed in mature lymphocytes, i.e. memory B cells, plasmablasts and bone marrow plasma cells. BCMA is also expressed on multiple myeloma cells.

Although BCMA is a promising target antigen for the treatment of multiple myeloma, traditional targeting approaches are hampered by the low density of expression of BCMA on myeloma cells. Consequently, it is unlikely that a traditional therapeutic antibody will achieve sufficient density on the myeloma cell surface to trigger efficient ADCC/CDC. Similarly, a conjugate of a mAb with a toxin or chemotherapeutic is unlikely to result in a useful therapeutic window given the small differential between targeted and non-specific uptake.

Thus there is need for alternative agents which can discriminate low BCMA density into an effective therapeutic action.

BAFF interacts with TNF Receptor Superfamily Member 13C (BAFF-R), BCMA and TNF Receptor Superfamily Member 13B (TACI) while APRIL interacts with BCMA, TACI and proteoglycans. BAFF-R activation affects peripheral B-cell survival, while BCMA may affect plasma cell survival. APRIL interaction with proteoglycans involves acidic sulphated glycol-saminoglycan side-chains amino-terminus of APRIL FIG. 2 A: Different formats designed and constructed
(1) OKT3 scFv connected to truncated APRIL by the IgG1 hinge; (2) OKT3 scFv connected to truncated APRIL via a (SGGGGS)3 (SEQ ID No. 22) linker; (3) OKT3 scFv connected to truncated APRIL via the CD8 stalk; (4) truncated APRIL connected to OKT3 scFv via an IgG1 hinge; (5) truncated APRIL connected to the OKT3 scFv via a (SGGGGS)$_3$ (SEQ ID No. 22) linker; (6) truncated APRIL connected to the OKT3 scFv via a CD8 spacer. Constructs (3) and (6) should form homodimers through disulphide bonds in the CD8 spacer. (HNG=Hinge, STK=Stalk)

B: schematic diagram of molecular clustering on the cell-to-cell interface upon binding of the APRILiTE.

Figure 3:
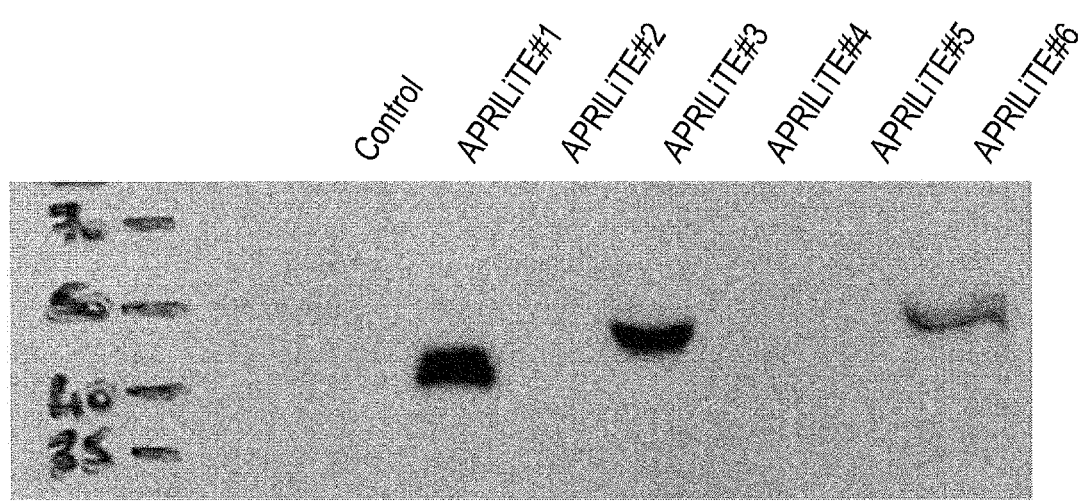

FIG. 3—Western blot of supernatant from 293T cells transfected with the different APRILiTE constructs. Blotting was done with anti-APRIL.

Figure 4:
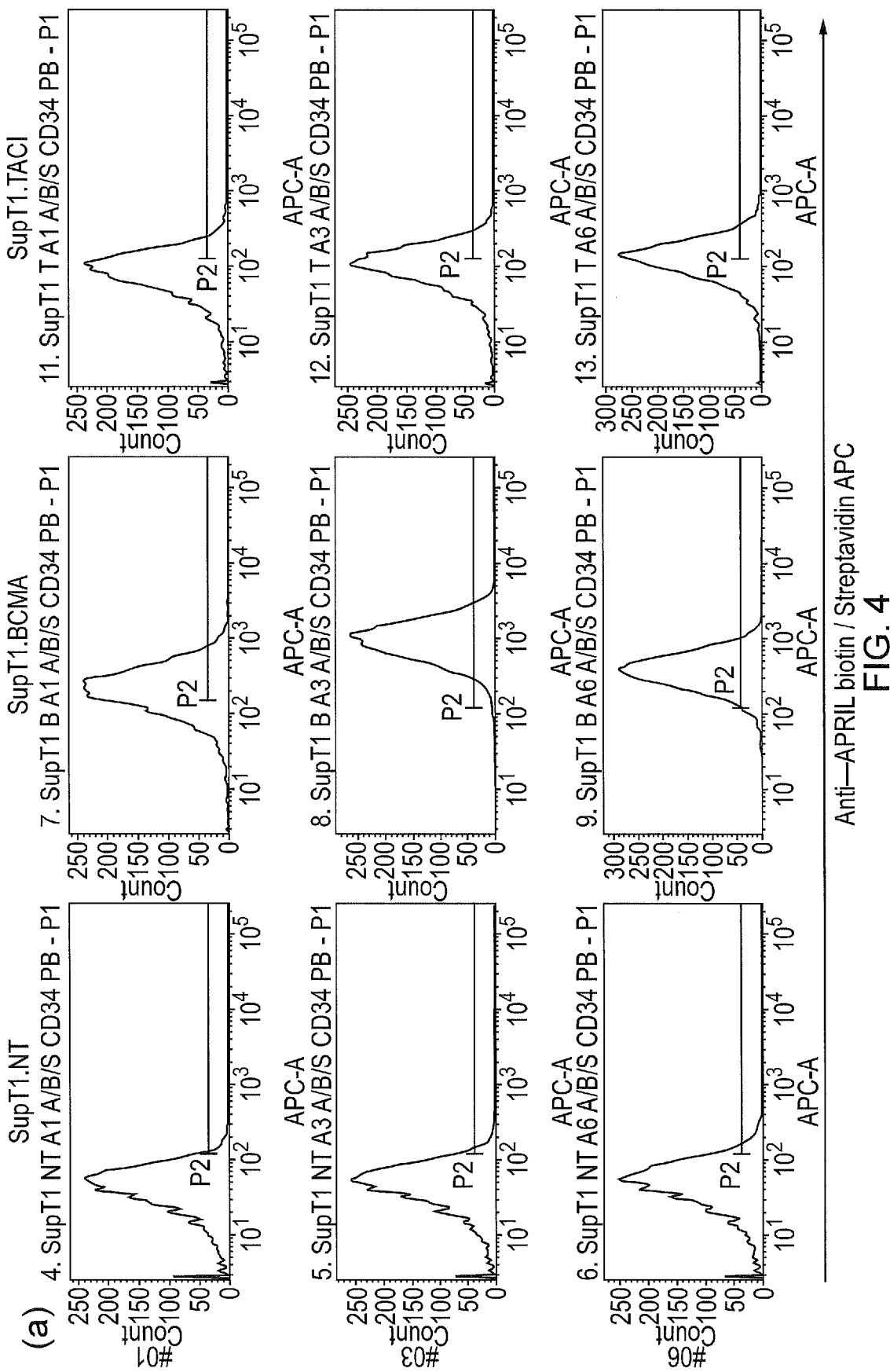
Figure 4:
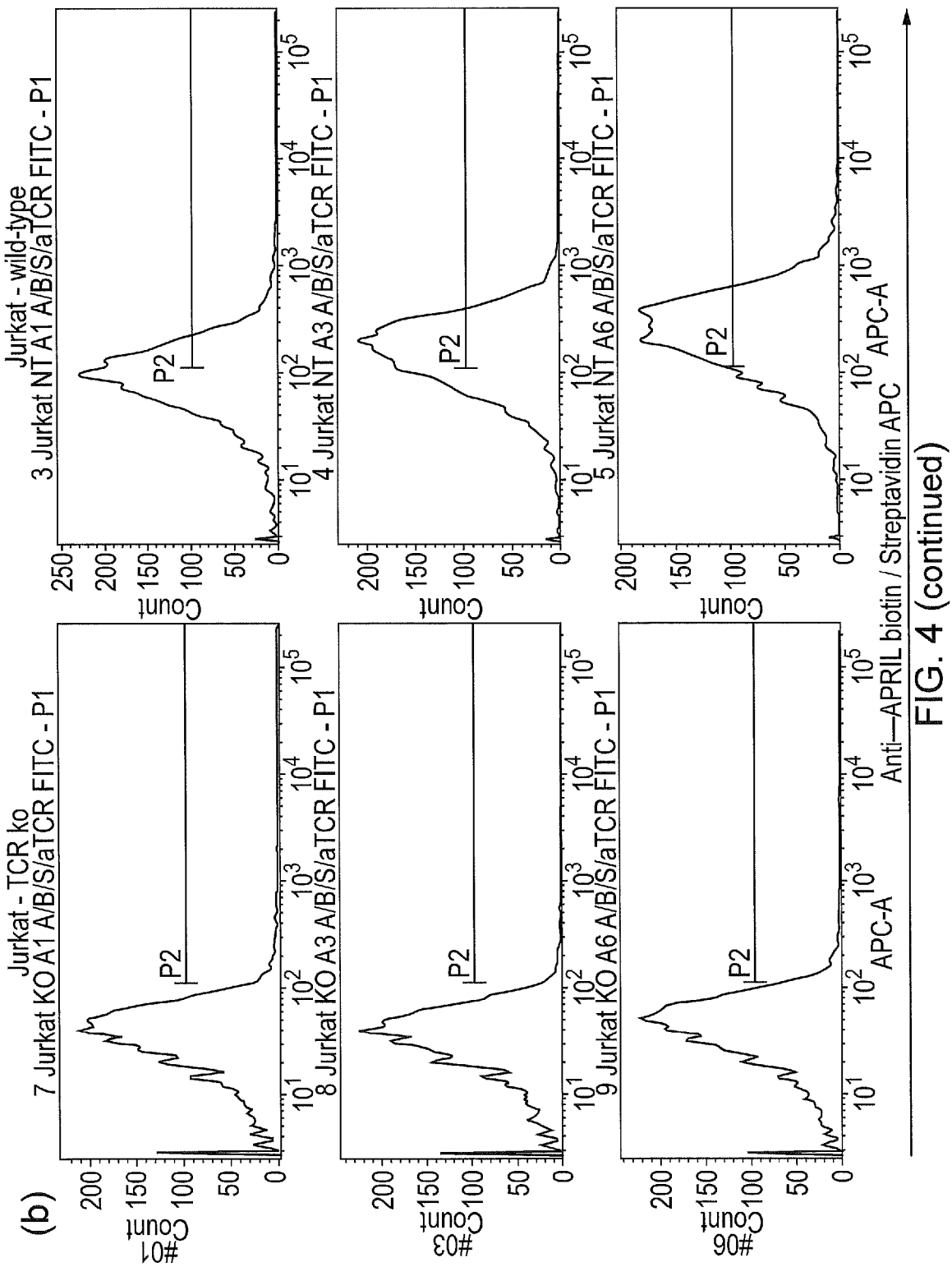

FIG. 4(a)—Binding of APRILiTES 1, 3 and 6 to wild-type SupT1 cells and SupT1 cells engineered to express BCMA and TACI. Staining is with anti-APRIL biotin/Streptavidin APC. Aprilites show no binding to WT SupT1 cells but bind to BCMA expressing cells, and to a lesser extent to TACI expressing cells.

FIG. 4(b)—Binding of APRILiTEs to wild-type Jurkats, but not to Jurkats with no T-cell receptor. This demonstrates that the APRILiTES bind the T-cell receptor.

Figure 5:
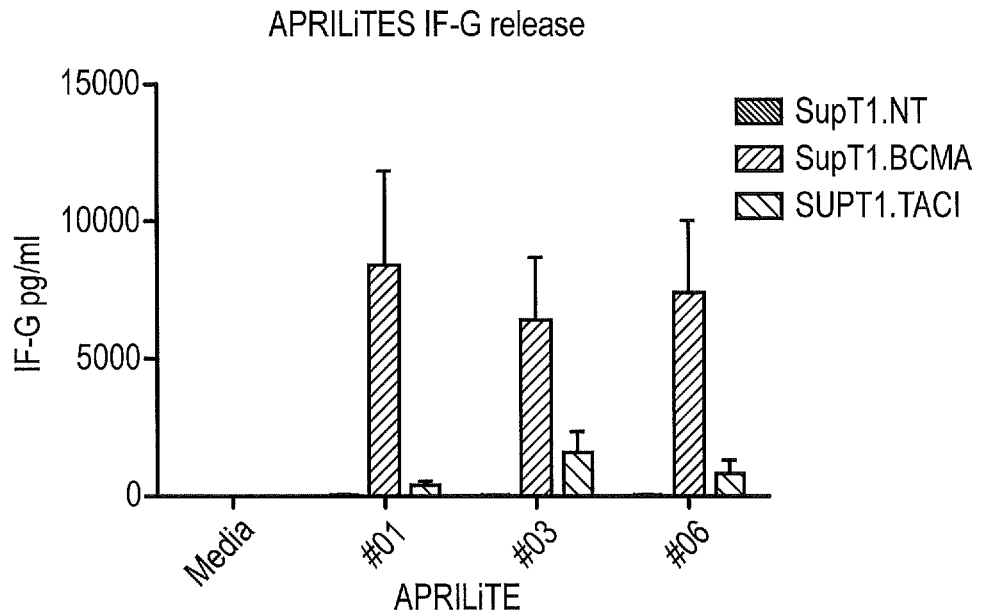

FIG. 5—Co-culture of T-cells 1:1 non-transduced or engineered SupT1 cells in the presence of blank media or the 3 APRILiTES.

Figure 6:
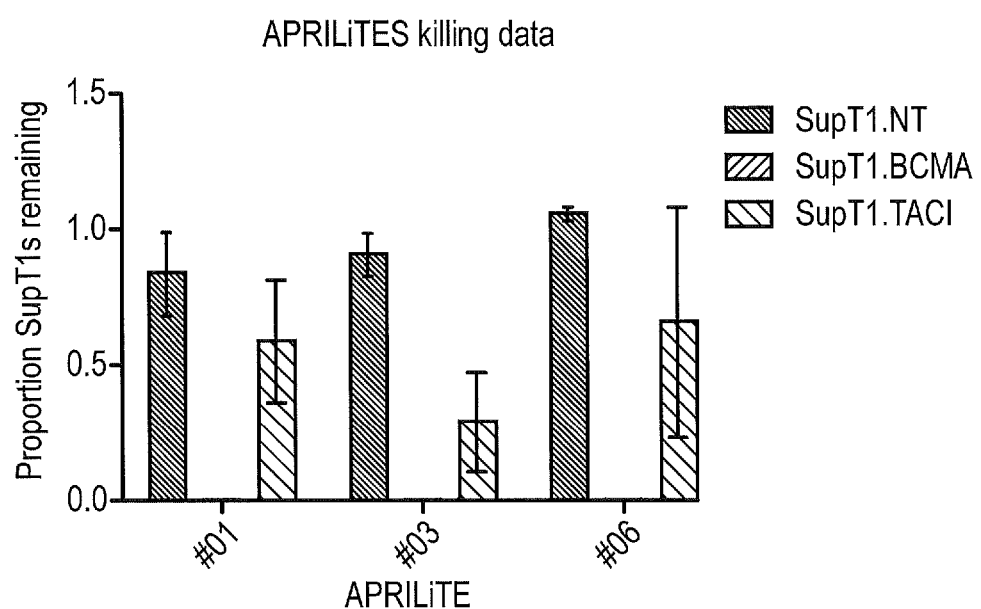

FIG. 6—Complete deletion of BCMA expressing SupT1 cells was observed after 3 day co-culture in the presence of APRILiTE 1,3 and 6.

Figure 7:
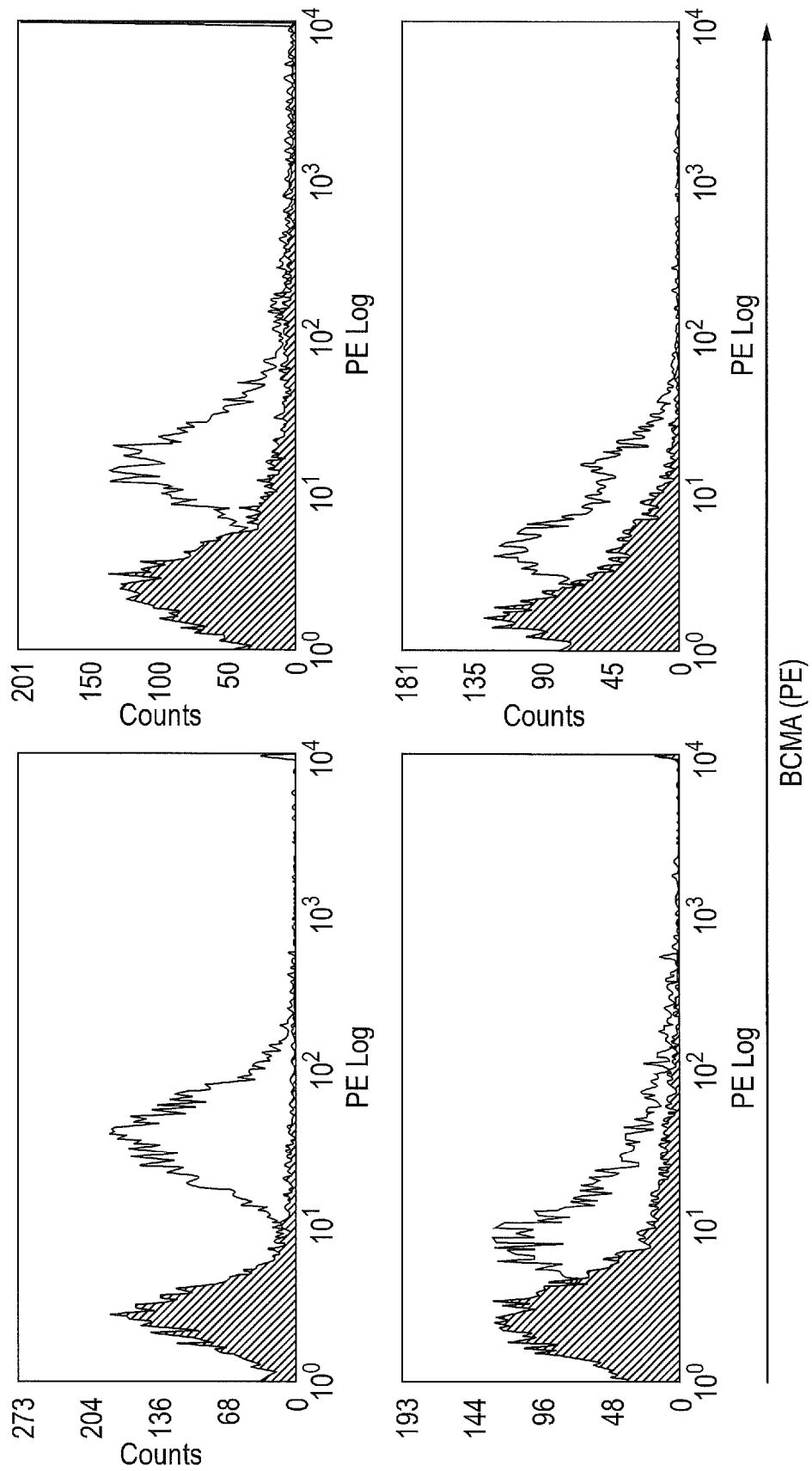

FIG. 7—Examples of BCMA expression on primary myelomas. Four examples of myeloma samples stained with the rat anti-human BCMA mAb Vicky1 is shown. The first panel shows bright BCMA staining in a patient with a plasma cell leukemia (an unusual, advanced and aggressive form of myeloma). The other three cases are clinically and morphologically typical myelomas. They show the intermediate or dim staining typically seen. Staining with isotype control (grey) is superimposed.

FIG. 8—Amino acid sequence of APRILiTEs
A: APRILiTE #01 (SEQ ID No. 10); B: APRILiTE #03 (SEQ ID No. 11); C: APRILiTE #06 (SEQ ID No. 12)

Figure 9:
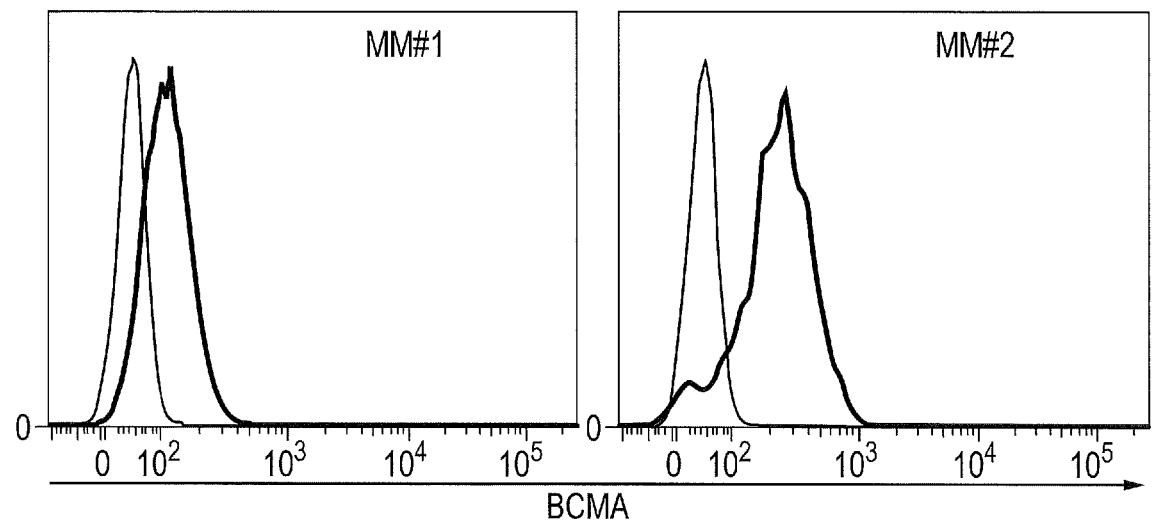

FIG. 9—Staining of myeloma samples for BCMA overlaid on isotype control. These myeloma cells express BCMA but at low levels FIG. 10—Low-power microscopy of co-cultures and controls at day 1. Clear clumping/activation of T-cells can be seen when cultured with myeloma cells in the presence of an APRILiTE.

Figure 11:
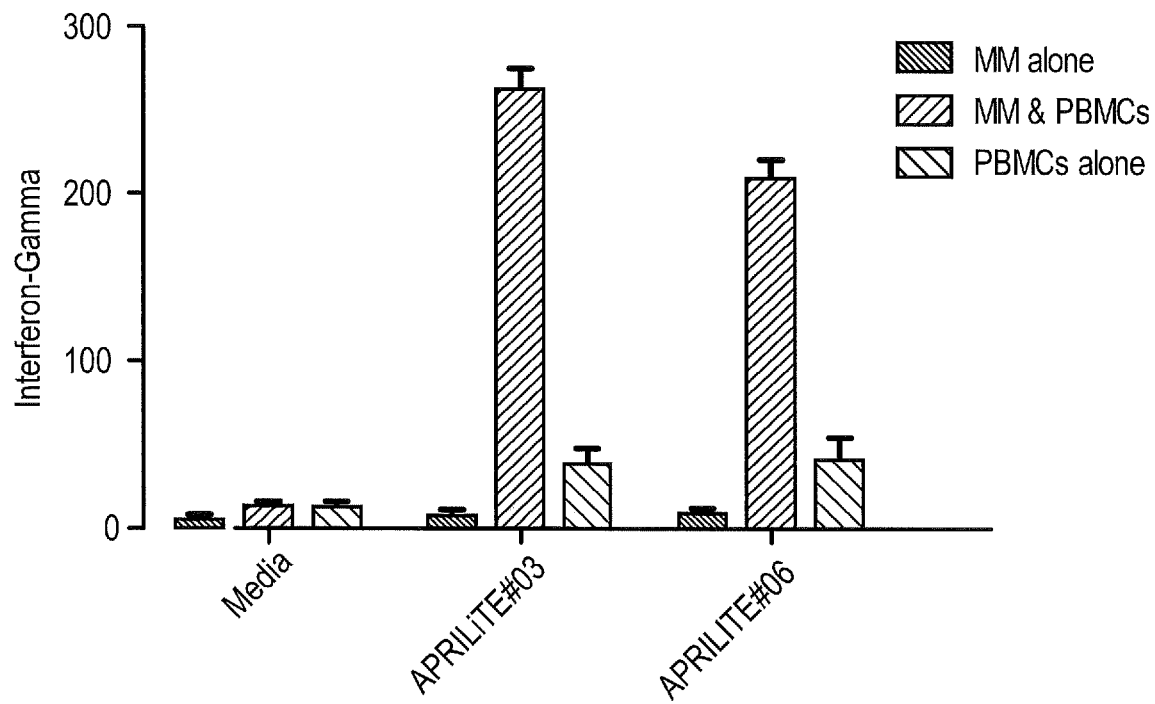

FIG. 11—Inteferon-gamma release with myeloma cells alone, co-cultured with peripheral blood T-cells, both together in the absence of and presence of APRILiTES #3 and #6

Figure 12:
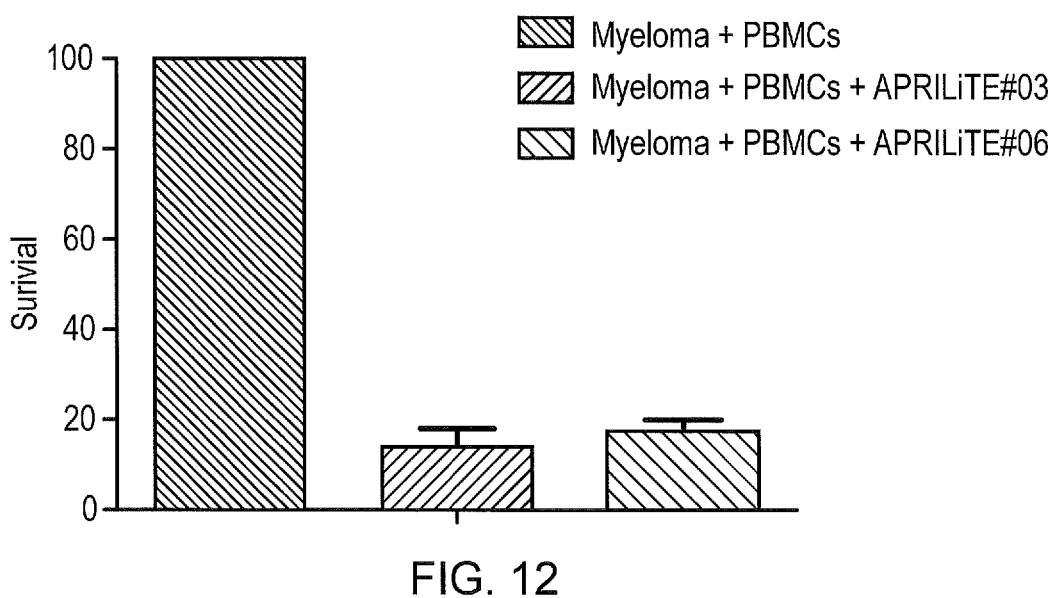

FIG. 12—Survival at day 6 of co-culture of myeloma cells in culture. Both APRILiTES tested result in efficient killing of primary myeloma cells in the presence of PBMCs.

SUMMARY OF ASPECTS OF THE INVENTION

B-cell membrane antigen (BCMA) is a surface protein expressed on nearly all Multiple Myeloma (MM). BCMA is only otherwise expressed on plasma cells hence targeting this antigen may prove an effective treatment of myeloma. However, the low-level expression of BCMA is a consideration when targeting this antigen.

The present inventors have surprisingly found that if a binding domain is used based on a proliferation-inducing ligand (APRIL), rather than a BCMA-binding antibody, in a bi-specific T cell activating (BTA) molecule, the molecule is capable of causing T-cell activation in the presence of myeloma cells.

Figure 2A:
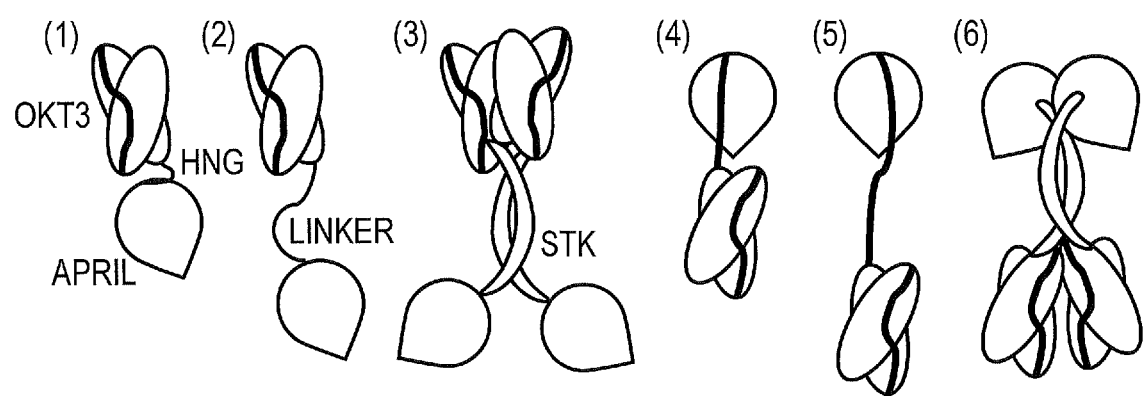
Figure 2B:
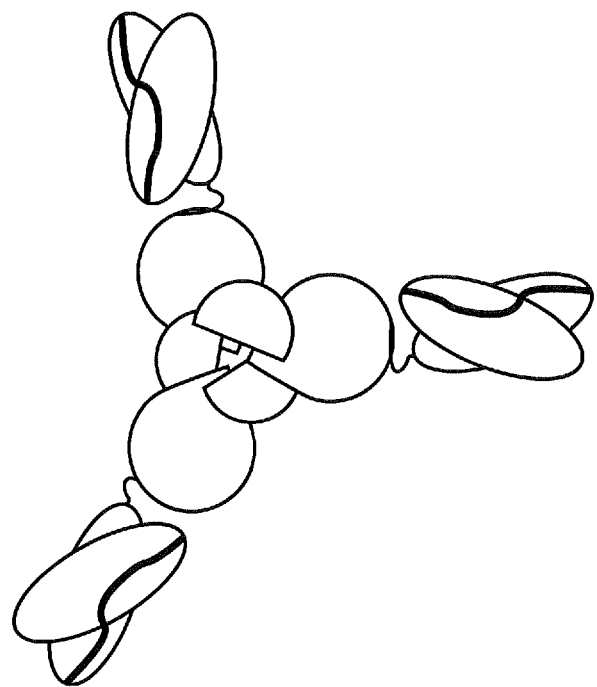

Without wishing to be bound by theory, the present inventors predict that this is because the bi-specific molecule of the invention binds BCMA with three-fold symmetry: i.e. an interaction between BCMA and the BTA of the invention requires trimerisation of each binding partner (see FIG. 2B). This induces clustering of T-cell activating domain at a protein level.

Using a traditional BiTE approach, T cell activation occurs only when a sufficient number of CD3/TCR complexes are engaged by the BiTE. This in turn is dependent on the antigen density on the target cell. Sufficient engagement must occur to overcome a threshold to trigger the T cell activating cascade. If engagement is insufficient, for instance because the level expression of target antigen is too low on the target cell, this threshold is not met and T-cell activation does not occur.

With the bispecific molecule of the present invention, BCMA molecule expression on the target cell, causes three bi-specific molecules of the present invention to cluster, providing three CD3-binding domains for T-cell activation. In embodiment where the bispecific molecule of the invention exists as a homodimer (for example the embodiment which comprises a CD8 stalk, see FIG. 2(*a*)(3)) the BTA can recruit 2 CD3/TCR complex for every BCMA engaged increasing this signal amplification further. This stoichiometry is sufficient to provide the threshold level of CD3 binding to lead to T cell activation.

Thus, in a first aspect the present invention provides a bi-specific molecule which comprises:
(i) a first domain which binds B cell maturation antigen (BCMA) and comprises at least part of a proliferation-inducing ligand (APRIL); and
(ii) a second domain capable of activating a T cell.

The second domain may activate a T cell by binding CD3 on the T-cell surface. In this respect, the second domain may comprise a CD3 or TCR-specific antibody or part thereof.

The second domain may comprise the complementarity determining regions (CDRs) from the scFv sequence shown as SEQ ID No. 9.

The second domain may comprise a scFv sequence, such as the one shown as SEQ ID No. 9. The second domain may comprise a variant of such a sequence which has at least 80% sequence identity and binds CD3.

The first domain may comprise a truncated APRIL which comprises the BCMA binding site but lacks the amino terminal portion of APRIL responsible for proteoglycan binding. Such a molecule may comprise the sequence shown as SEQ ID No. 2. Alternatively the molecule may comprise a variant of that sequence having at least 80% sequence identity which binds BCMA.

The first and second binding domains may be connected by a spacer, such as a spacer which comprises an IgG1 hinge, a serine-glycine linker or a CD8 stalk.

The spacer may cause the BTA to form a homodimer, for example due to the presence of one or more cysteine residues in the spacer, which can for a di-sulphide bond with another molecule comprising the same spacer.

The bi-specific molecule may comprise the sequence shown as SEQ ID No. 10, 11 or 12 or a variant thereof which has at least 80% sequence identity but retains the capacity to i) bind BCMA and ii) activate a T cell.

The bi-specific molecule may bind to BCMA, such a BCMA on the surface of a plasma cell, as a trimer.

In a second aspect, the present invention provides a nucleic acid sequence which encodes a bi-specific molecule according to the first aspect of the invention.

The nucleic acid sequence may comprise the sequence shown as SEQ ID No 19, 20 or 21 or a variant thereof having at least 80% sequence identity.

In a third aspect, the present invention provides a vector which comprises a nucleic acid sequence according to the second aspect of the invention.

In a fourth aspect, the present invention provides a host cell which comprises a nucleic acid sequence according to the second aspect of the invention and produces a bi-specific molecule according to the first aspect of the invention.

In a fifth aspect, the present invention provides a method for producing a bi-specific molecule according to the first aspect of the invention which comprises the step of culturing a host cell according to the fourth aspect of the invention under conditions such that the bi-specific molecule is produced.

In a sixth aspect, the present invention provides a pharmaceutical composition which comprises a bi-specific molecule according to the first aspect of the invention, together with a pharmaceutically acceptable carrier, diluent or excipient.

In a seventh aspect, the present invention provides a method for treating a plasma cell disorder which comprises the step of administering a bi-specific molecule according to the first aspect of the invention to a subject.

The plasma cell disorder may, for example be plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma, heavy chain diseases, monoclonal gammopathy of undetermined significance or smoldering multiple myeloma.

The plasma cell disorder may be multiple myeloma.

In an eighth aspect, the present invention provides a bi-specific molecule according to the first aspect of the invention for use in treating a plasma cell disorder.

In a ninth aspect, the present invention provides the use of a bi-specific molecule according to the first aspect of the invention the manufacture of a medicament for treating a plasma cell disorder.

In a tenth aspect, the present invention provides a bi-specific molecule which comprises a first binding domain and a second binding domain, wherein the first and second binding domains are connected by a spacer which is or comprises a CD8 stalk.

DETAILED DESCRIPTION

B-Cell Membrane Antigen (BCMA)

The bi-specific molecule of the first aspect of the invention comprises a first domain which binds B cell maturation antigen (BCMA).

BCMA, also known as TNFRSF17, is a plasma cell specific surface antigen which is expressed exclusively on B-lineage haemopoietic cells or dendritic cells. It is a member of the TNF receptor family. BCMA is not expressed on nave B cells but is up-regulated during B-cell differentiation into plasmablasts, and is brightly expressed on memory B cells, plasmablasts and bone marrow plasma cells. BCMA is also expressed on the majority of primary myeloma cells.

Figure 1:
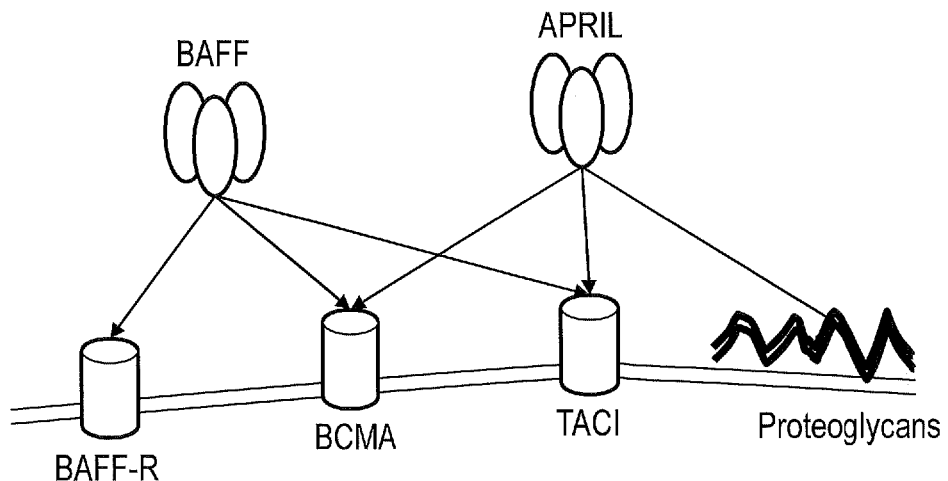
FIG. 1—Ligand Specificity and Function Assignment of TNF Superfamily Member 13C (BAFF) and A proliferation-inducing ligand (APRIL)/TNF Superfamily Member 13 Protein (TNFSF13)

BCMA functions within a network of interconnected ligands and receptors which is shown schematically in FIG. 1. Two other TNF receptors share the ligands APRIL and BAFF with BCMA—TACI (TNFRSFI3B), which is found on activated T-cells and all B-cells and BAFF-R (TNFRSF13C) which is predominantly expressed on B-lymphocytes. Multiple myeloma cells express TACI in some cases and BCMA in most cases, but never BAFF-R.

APRIL

The first domain of the bi-specific molecule of the invention and comprises at least part of a proliferation-inducing ligand (APRIL). APRIL is also known as TNFSFI3.

The wild-type sequence of APRIL is available at UNIPROT/O75888 and is show below (SEQ ID No. 1). It is not a classical secreted protein in that it has no signal peptide. It has a furin cleavage site "KQKKQK" (SEQ ID No. 23) (underlined in SEQ ID No. 1). The amino terminus is involved in proteoglycan binding.

The first binding domain may comprise the BCMA-binding site of APRIL. The first binding domain may comprise a fragment of APRIL which comprises the BCMA-binding site.

The first binding domain may comprise a truncated APRIL, which lacks the amino terminal end of the molecule. The truncated APRIL may retain BCMA and TACI binding but lose proteoglycan binding. Truncated APRIL can be cleaved at or immediately after the furin cleavage site. Truncated APRIL may lack the amino terminal 116 amino acids from the wild-type APRIL molecule shown as SEQ ID No. 2. Truncated APRIL may comprise the sequence shown as SEQ ID No. 2 (which corresponds to the portion of SEQ ID No. 1 shown in bold) or a variant thereof. This corresponds to the portion of the molecule which is needed for BCMA and TACI binding.

```
                                        SEQ ID No. 1
         10          20          30          40
MPASSPFLLA PKGPPGNMGG PVREPALSVA LWLSWGAALG 50          60          70          80
AVACAMALLT QQTELQSLRR EVSRLQGTGG PSQNGEGYPW 90         100         110         120
QSLPEQSSDA LEAWENGERS RKRRAVLTQK QKKQHSVLHL 130         140         150         160
VPINATSKDD SDVTEVMWQP ALRRGRGLQA QGYGVRIQDA 170         180         190         200
GVYLLYSQVL FQDVTFTMGQ VVSREGQGRQ ETLFRCIRSM 210         220         230         240
PSHPDRAYNS CYSAGVFHLH QGDILSVIIP RARAKLNLSP

250
HGTFLGFVKL
```

```
                                        SEQ ID No. 2
VLHLVPINATSKDDSDVTEVMWQPALRRGRGLQAQGYGVRIQDAGVYLLY
SQVLFQDVTFTMGQWSREGQGRQETLFRCIRSMPSHPDRAYNSCYSAGVF
HLHQGDILSVIIPRARAKLNLSPHGTFLGFVKL
```

The bi-specific molecule of the present invention may comprise a variant of the truncated APRIL molecule shown as SEQ ID No. 2 which has at least 80% amino acid sequence identity and which has the same or improved BCMA binding capabilities. The variant sequence may have at least 80%, 85%, 90%, 95%, 98% or 99% sequence identity to SEQ ID No. 2.

The percentage identity between two polypeptide sequences may be readily determined by programs such as BLAST which is freely available at http://blast.ncbi.nlm.nih.gov.

T Cell Activation

The second domain of the molecule of the present invention is capable of activating T cells. T cells have a T cell-receptor (TCR) at the cell surface which recognises antigenic peptides when presented by an MHC molecule on the surface of an antigen presenting cell. Such antigen recognition results in the phosphorylation of immunoreceptor tyrosine-based activation motifs (ITAMs) by Src family kinases, triggering recruitment of further kinases which results in T cell activation including $Ca^{2+}$ release.

The second domain may cause T cell activation by triggering the same pathway triggered by antigen-specific recognition by the TCR.

Cluster Of Differentiation 3 (CD3)

The second domain of the bi-specific molecule of the invention may bind CD3.

CD3 is a protein complex composed of four distinct chains: a CD3γ chain, a CD3δ chain, and two CD3ε chains. CD3 associates with the T-cell receptor (TCR) and the ζ-chain on the surface of a T cell to generate an activation signal. The TCR, ζ-chain, and CD3 molecule together comprise the TCR complex.

Clustering of CD3 on T cells, e.g. by immobilized anti-CD3-antibodies, leads to T cell activation similar to the engagement of the T cell receptor, but independent from its clone typical specificity.

Due to its central role in modulating T cell activity, there have been attempts to develop molecules that are capable of binding TCR/CD3. Much of this work has focused on the generation of antibodies that are specific for the human CD3 antigen.

The second domain may comprise an antibody or part thereof which specifically binds CD3, such as OKT3, WT32, anti-leu-4, UCHT-1, SPV-3TA, TR66, SPV-T3B or affinity tuned variants thereof.

As used herein, "antibody" means a polypeptide having an antigen binding site which comprises at least one complementarity determining region CDR. The antibody may comprise 3 CDRs and have an antigen binding site which is equivalent to that of a domain antibody (dAb). The antibody may comprise 6 CDRs and have an antigen binding site which is equivalent to that of a classical antibody molecule. The remainder of the polypeptide may be any sequence which provides a suitable scaffold for the antigen binding site and displays it in an appropriate manner for it to bind the antigen. The antibody may be a whole immunoglobulin molecule or a part thereof such as a Fab, F(ab)'$_2$, Fv, single chain Fv (ScFv) fragment, Nanobody or single chain variable domain (which may be a VH or VL chain, having 3 CDRs). The antibody may be a bifunctional antibody. The antibody may be non-human, chimeric, humanised or fully human.

Alternatively the second domain may comprise a CD3-binding molecule which is not derived from or based on an immunoglobulin. A number of "antibody mimetic" designed repeat proteins (DRPs) have been developed to exploit the binding abilities of non-antibody polypeptides. Such molecules include ankyrin or leucine-rich repeat proteins e.g. DARPins (Designed Ankyrin Repeat Proteins), Anticalins, Avimers and Versabodies.

The second domain of the bi-specific molecule of the invention may comprise all or part of the monoclonal antibody OKT3, which was the first monoclonal antibody approved by the FDA. OKT3 is available from ATCC CRL 8001. The antibody sequences are published in U.S. Pat. No. 7,381,803.

The second domain may comprise one or more CDRs from OKT3. The second binding domain may comprise CDR3 from the heavy-chain of OKT3 and/or CDR3 from the light chain of OKT3. The second binding domain may comprise all 6 CDRs from OKT3, as shown below.

Heavy Chain

```
                              (SEQ ID No. 3)
       CDR1: KASGYTFTRYTMH (SEQ ID No. 4)
       CDR2: INPSRGYTNYNQKFKD (SEQ ID No. 5)
       CDR3: YYDDHYCLDY
```

Light Chain

```
                              (SEQ ID No. 6)
       CDR1: SASSSVSYMN (SEQ ID No. 7)
       CDR2: RWIYDTSKLAS (SEQ ID No. 8)
       CDR3: QQWSSNPFT
```

The second binding domain may comprise a scFv which comprises the CDR sequences from OKT3. The second binding domain may comprise the scFv sequence shown below as SEQ IN No. 9 or a variant thereof having at least 80% sequence identity, which retains the capacity to bind CD3.

```
                                             SEQ ID No. 9
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSSGGGGSGGGGSGGGGSQIVLTQSPAIMSASP

GEKVTMTCSASSSVSYMNWYQQKSGTSPKRWIYDTSKLASGVPAHFRGSG

SGTSYSLTISGMEAEDAATYYCQQWSSNPFTFGSGTKLEINR
```

A variant sequence from SEQ ID No. 9 may have at least 80, 85, 90, 95, 98 or 99% sequence identity and have equivalent or improved CD3 binding and/or TCR activation capabilities as the sequence shown as SEQ ID No. 9.

Bi-Specific T-Cell Engagers (BITES)

BiTES are a new class of therapeutics which approximate a target antigen with the T-cell receptor (TCR). The original design was of two scFvs connected together by a linker with one scFv targeting antigen and the other activating a T-cell.

BiTEs are commonly made by fusing an anti-CD3 scFv to an anti-target antigen scFv via a short five residue peptide linker (GGGGS, SEQ ID No. 24). In 1995, a tandem scFv targeting EpCAM (epithelial 17-1A antigen) and human CD3 in CHO cells was produced. This new kind of bi-specific antibody format proved to be highly cytotoxic at nanomolar concentrations against various cell lines, using unstimulated human PBMCs in the absence of co-signaling. Later, a fusion between a murine anti-CD19 scFv and a murine anti-CD3 scFv was created. This molecule demonstrated outstanding in vitro properties, including efficient cytotoxicity, without the need of co-signaling (e.g., through CD28).

Blinatumomab, a murine anti-human CD3×anti-human CD19 was the first BiTE developed and is the most advanced BiTE in clinical trials. The candidate is being studied as a treatment of lymphoma and leukemia.

MT110, an anti-human EpCAM×anti-human CD3 TaFv, was the second BiTE tested in clinical trial and the first directed to a wide spectrum of solid tumors. In vitro characterizations of MT110 have recapitulated the results obtained with MT103 on tumor cell lines, thereby demonstrating the generality of the BiTE format. MT110 is currently in clinical trial for lung, colorectal and gastrointestinal cancer patients.

The bi-specific molecule of the present invention is based on a BiTE-like format, but instead of having a scFv or other antibody-based binding domain binding the target antigen, it has a binding domain based on the ligand for BCMA, namely APRIL.

This "APRILiTE" format is favourable compared with a classical scFv-scFv format for various reasons: (a) a single domain—scFv fusion is likely more stable and easier to make than other formats; (b) the assembly of BCMA and APRIL on the cell surface require trimerization of each binding partner. This induces clustering of T-cell activating domain at a protein level making the protein highly specific and highly potent.

The molecule of the present invention may comprise one of the following amino acid sequences:

SEQ ID No. 10
METDTLLLWVLLLWVPGSTGQVQLQQSGAELARPGASVKMSCKASGYTFT
RYTMHWVKQRPGQGLEWIGYINPSRGYTNYNQKFKDKATLTTDKSSSTAY
MQLSSLTSEDSAVYYCARYYDDHYCLDYWGQGTTLTVSSSGGGGSGGGGS
GGGGSQIVLTQSPAIMSASPGEKVTMTCSASSSVSYMNWYQQKSGTSPKR
WIYDTSKLASGVPAHFRGSGSGTSYSLTISGMEAEDAATYYCQQWSSNPF
TFGSGTKLEINRSDPAEPKSPDKTHTCPPCPKDPKSGGGGSVLHLVPINA
TSKDDSDVTEVMWQPALRRGRGLQAQGYGVRIQDAGVYLLYSQVLFQDVT
FTMGQVVSREGQGRQETLFRCIRSMPSHPDRAYNSCYSAGVFHLHQGDIL
SVIIPRARAKLNLSPHGTFLGFVKL

SEQ ID No. 11
METDTLLLWVLLLWVPGSTGQVQLQQSGAELARPGASVKMSCKASGYTFT
RYTMHWVKQRPGQGLEWIGYINPSRGYTNYNQKFKDKATLTTDKSSSTAY
MQLSSLTSEDSAVYYCARYYDDHYCLDYWGQGTTLTVSSSGGGGSGGGGS
GGGGSQIVLIQSPAIMSASPGEKVTMTCSASSSVSYMNWYQQKSGTSPKR
WIYDTSKLASGVPAHFRGSGSGTSYSLTISGMEAEDAATYYCQQWSSNPF
TFGSGTKLEINRSDPTTTPAPRPPTPAPTIASQPLSLRPEACRPAAGGAV
HTRGLDFACDSGGGGSVLHLVPINATSKDDSDVTEVMWQPALRRGRGLQA
QGYGVRIQDAGVYLLYSQVLFQDVTFTMGQVVSREGQGRQETLFRCIRSM
PSHPDRAYNSCYSAGVFHLHQGDILSVIIPRARAKLNLSPHGTFLGFVKL

SEQ ID No. 12
MGTSLLCWMALCLLGADHADGVLHLVPINATSKDDSDVTEVMWQPALRRG
RGLQAQGYGVRIQDAGVYLLYSQVLFQDVTFTMGQVVSREGQGRQETLFR
CIRSMPSHPDRAYNSCYSAGVFHLHQGDILSVIIPRARAKLNLSPHGTFL
GFVKLSGGGSDPTTTPAPRPPTPAPTIASQPLSLRPEACRPAAGGAVHTR
GLDFACDSGGGGSQVQLQQSGAELARPGASVKMSCKASGYTFTRYTMHWV
KQRPGQGLEWIGYINPSRGYTNYNQKFKDKATLTTDKSSSTAYMQLSSLT
SEDSAVYYCARYYDDHYCLDYWGQGTTLTVSSSGGGGSGGGGSGGGGSQI
VLTQSPAIMSASPGEKVTMTCSASSSVSYMNVVYQQKSGTSPKRWIYDTS
KLASGVPAHFRGSGSGTSYSLTISGMEAEDAATYYCQQWSSNPFTFGSGT
KLEINRS

The molecule of the invention may comprise a variant of the sequence shown as SEQ ID No. 10, 11 or 12 having at least 80, 85, 90, 95, 98 or 99% sequence identity, provided that the variant sequence is a molecule as defined in the first aspect of the invention, i.e. a bi-specific molecule which comprises:
(i) a first domain which binds B cell maturation antigen (BCMA) and comprises at least part of a proliferation-inducing ligand (APRIL); and
(ii) a second domain capable of activating a T cell.

Signal Peptide

The bi-specific molecule of the invention may comprise a signal peptide to aid in its production. The signal peptide may cause the bi-specific molecule to be secreted by a host cell, such that the bi-specific molecule can be harvested from the host cell supernatant.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The bi-specific molecule may have the general formula:

Signal peptide-first domain-second domain.

The signal peptide may comprise the SEQ ID No. 13 or 14 or a variant thereof having 5, 4, 3, 2 or 1 amino acid mutations (insertions, substitutions or additions) provided that the signal peptide still functions to cause secretion of the bi-specific molecule.

SEQ ID No. 13: METDTLLLWVLLLWVPGSTG

SEQ ID No. 14: MGTSLLCWMALCLLGADHADG

The signal peptides of SEQ ID No. 13 and 14 are compact and highly efficient. They are predicted to give about 95% cleavage after the terminal glycine, giving efficient removal by signal peptidase.

Spacer

The molecule of the present invention may comprise a spacer sequence to connect the first domain with the second domain and spatially separate the two domains.

The spacer sequence may, for example, comprise an IgG1 hinge or a CD8 stalk. The linker may alternatively comprise an alternative linker sequence which has similar length and/or domain spacing properties as an IgG1 hinge or a CD8 stalk.

The spacer may be a short spacer, for example a spacer which comprises less than 100, less than 80, less than 60 or less than 45 amino acids. The spacer may be or comprise an IgG1 hinge or a CD8 stalk or a modified version thereof.

Examples of amino acid sequences for these linkers are given below:

SEQ ID No. 15
(IgG1 hinge):
AEPKSPDKTHTCPPCPKDPKSGGGGS

SEQ ID No. 16
(CD8 stalk):
TTTPAPRPPTPAPTIASQPLSLRPEACRPAAGGAVHTRGLDFACD

The CD8 stalk has a sequence such that it may induce the formation of homodimers (see FIG. 2). If this is not desired, one or more cysteine residues may be substituted or removed from the CD8 stalk sequence. The bispecific molecule of the invention may include a spacer which comprises or consists of the sequence shown as SEQ ID No. 16 or a variant thereof having at least 80, 85, 90, 95, 98 or 99% sequence identity, provided that the variant sequence is a molecule which causes approximately equivalent spacing of the first and second domains and/or that the variant sequence causes homodimerisation of the bi-specific molecule.

The molecule of the invention may have the general formula:

Signal peptide-first domain-spacer-second domain.

The spacer may also comprise one or more linker motifs to introduce a chain-break. A chain break separate two distinct domains but allows orientation in different angles.

Such sequences include the sequence SDP, and the sequence SGGGSDP (SEQ ID No. 17).

The linker may comprise a serine-glycine linker, such as SGGGS (SEQ ID No. 18).

Nucleic Acid Sequence

The second aspect of the invention relates to a nucleic acid sequence which codes for a bi-specific molecule of the first aspect of the invention.

The nucleic acid sequence may be or comprise one of the following sequences:

SEQ ID No. 19
(APRILiTE#01)
ATGGAGACCGACACCCTGCTGCTGTGGGTGCTGCTGCTGTGGGTGCCAGG
CAGCACCGGCCAGGTGCAGCTGCAGCAGAGCGGAGCCGAGCTGGCCAGAC
CAGGCGCCAGCGTGAAGATGAGCTGCAAGGCCAGCGGCTACACCTTCACC
CGGTACACCATGCACTGGGTGAAGCAGCGGCCAGGCCAGGGCCTGGAGTG
GATCGGCTACATCAACCCCAGCAGAGGCTACACCAACTACAACCAGAAGT
TCAAGGACAAGGCCACCCTGACCACCGACAAGAGCAGCAGCACCGCCTAC
ATGCAGCTGAGCAGCCTGACCAGCGAGGACAGCGCCGTGTACTACTGCGC
CAGATACTACGACGACCACTACTGCCTGGACTACTGGGGCCAGGGCACCA
CCCTGACCGTGAGCAGCTCTGGCGGAGGCGGCTCTGGCGGAGGCGGCTCT
GGCGGAGGCGGCAGCCAGATCGTGCTGACCCAGAGCCCAGCCATCATGAG
CGCCAGCCCAGGCGAGAAGGTGACCATGACCTGCAGCGCCAGCAGCAGCG
TGAGCTACATGAACTGGTACCAGCAGAAGAGCGGCACCAGCCCCAAGCGG
TGGATCTACGACACCAGCAAGCTGGCCAGCGGCGTGCCAGCCCACTTCAG
AGGCAGCGGCAGCGGCACCAGCTACAGCCTGACCATCAGCGGCATGGAGG
CCGAGGATGCCGCCACCTACTACTGCCAGCAGTGGAGCAGCAACCCCTTC
ACCTTCGGCAGCGGCACCAAGCTGGAGATCAACCGGTCGGATCCCGCCGA
GCCCAAATCTCCTGACAAAACTCACACATGCCCACCGTGCCCAAAAGATC
CCAAATCTGGCGGAGGCGGCAGCGTGCTGCACCTGGTGCCCATCAACGCC
ACCAGCAAGGACGACTCTGATGTGACCGAGGTGATGTGGCAGCCAGCCCT
GAGACGGGGCAGAGGCCTGCAGGCCCAGGGCTACGGCGTGAGAATCCAGG
ACGCTGGCGTGTACCTGCTGTACTCCCAGGTGCTGTTCCAGGACGTGACC
TTCACAATGGGCCAGGTGGTGAGCCGGGAGGGCCAGGGCAGACAGGAGAC
CCTGTTCCGGTGCATCCGGAGCATGCCCAGCCACCCCGACAGAGCCTACA
ACAGCTGCTACAGCGCTGGCGTGTTTCACCTGCACCAGGGCGACATCCTG
AGCGTGATCATCCCCAGAGCCAGAGCCAAGCTGAACCTGTCCCCCCACGG
CACCTTTCTGGGCTTCGTGAAGCTGTGA

SEQ ID No. 20
(APRILiTE#03)
ATGGAGACCGACACCCTGCTGCTGTGGGTGCTGCTGCTGTGGGTGCCAGG
CAGCACCGGCCAGGTGCAGCTGCAGCAGAGCGGAGCCGAGCTGGCCAGAC
CAGGCGCCAGCGTGAAGATGAGCTGCAAGGCCAGCGGCTACACCTTCACC
CGGTACACCATGCACTGGGTGAAGCAGCGGCCAGGCCAGGGCCTGGAGTG
GATCGGCTACATCAACCCCAGCAGAGGCTACACCAACTACAACCAGAAGT
TCAAGGACAAGGCCACCCTGACCACCGACAAGAGCAGCAGCACCGCCTAC
ATGCAGCTGAGCAGCCTGACCAGCGAGGACAGCGCCGTGTACTACTGCGC
CAGATACTACGACGACCACTACTGCCTGGACTACTGGGGCCAGGGCACCA
CCCTGACCGTGAGCAGCTCTGGCGGAGGCGGCTCTGGCGGAGGCGGCTCT
GGCGGAGGCGGCAGCCAGATCGTGCTGACCCAGAGCCCAGCCATCATGAG
CGCCAGCCCAGGCGAGAAGGTGACCATGACCTGCAGCGCCAGCAGCAGCG
TGAGCTACATGAACTGGTACCAGCAGAAGAGCGGCACCAGCCCCAAGCGG
TGGATCTACGACACCAGCAAGCTGGCCAGCGGCGTGCCAGCCCACTTCAG
AGGCAGCGGCAGCGGCACCAGCTACAGCCTGACCATCAGCGGCATGGAGG
CCGAGGATGCCGCCACCTACTACTGCCAGCAGTGGAGCAGCAACCCCTTC
ACCTTCGGCAGCGGCACCAAGCTGGAGATCAACCGGTCGGATCCCACCAC
GACGCCAGCGCCGCGACCACCAACACCGGCGCCCACCATCGCGTCGCAGC
CCCTGTCCCTGCGCCCAGAGGCGTGCCGGCCAGCGGCGGGGGCGCAGTG
CACACGAGGGGCTGGACTTCGCCTGTGATTCTGGCGGAGGCGGCAGCGT
GCTGCACCTGGTGCCCATCAACGCCACCAGCAAGGACGACTCTGATGTGA
CCGAGGTGATGTGGCAGCCAGCCCTGAGACGGGGCAGAGGCCTGCAGGCC
CAGGGCTACGCCGTGAGAATCCAGGACGCTGGCGTGTACCTGCTGTACTC
CCAGGTGCTGTTCCAGGACGTGACCTTCACAATGGGCCAGGTGGTGAGCC
GGGAGGGCCAGGGCAGACAGGAGACCCTGTTCCGGTGCATCCGGAGCATG
CCCAGCCACCCCGACAGAGCCTACAACAGCTGCTACAGCGCTGGCGTGTT
TCACCTGCACCAGGGCGACATCCTGAGCGTGATCATCCCCAGAGCCAGAG
CCAAGCTGAACCTGTCCCCCCACGGCACCTTTCTGGGCTTCGTGAAGCTG
TGA

SEQ ID No. 21
(APRILiTE#06)
ATGGGCACCTCCCTGCTGTGCTGGATGGCCCTGTGCCTGCTGGGAGCCGA
CCACGCCGACGGCGTGCTGCACCTGGTGCCCATCAACGCCACCAGCAAGG
ACGACTCTGATGTGACCGAGGTGATGTGGCAGCCAGCCCTGAGACGGGGC
AGAGGCCTGCAGGCCCAGGGCTACGGCGTGAGAATCCAGGACGCTGGCGT
GTACCTGCTGTACTCCCAGGTGCTGTTCCAGGACGTGACCTTCACAATGG
GCCAGGTGGTGAGCCGGGAGGGCCAGGGCAGACAGGAGACCCTGTTCCGG
TGCATCCGGAGCATGCCCAGCCACCCCGACAGAGCCTACAACAGCTGCTA
CAGCGCTGGCGTGTTTCACCTGCACCAGGGCGACATCCTGAGCGTGATCA
TCCCCAGAGCCAGAGCCAAGCTGAACCTGTCCCCCCACGGCACCTTTCTG
GGCTTCGTGAAGCTGTCTGGAGGCGGCTCGGATCCCACCACGACGCCAGC
GCCGCGACCACCAACACCGGCGCCCACCATCGCGTCGCAGCCCCTGTCCC
TGCGCCCAGAGGCGTGCCGGCCAGCGGCGGGGGCGCAGTGCACACGAGG
GGGCTGGACTTCGCCTGTGATAGCGGTGGCGGTGGCAGCCAGGTGCAGCT
GCAGCAGAGCGGAGCCGAGCTGGCCAGACCAGGCGCCAGCGTGAAGATGA
GCTGCAAGGCCAGCGGCTACACCTTCACCCGGTACACCATGCACTGGGTG

-continued

```
AAGCAGCGGCCAGGCCAGGGCCTGGAGTGGATCGGCTACATCAACCCCAG

CAGAGGCTACACCAACTACAACCAGAAGTTCAAGGACAAGGCCACCCTGA

CCACCGACAAGAGCAGCAGCACCGCCTACATGCAGCTGAGCAGCCTGACC

AGCGAGGACAGCGCCGTGTACTACTGCGCCAGATACTACGACGACCACTA

CTGCCTGGACTACTGGGGCCAGGGCACCACCCTGACCGTGAGCAGCTCTG

GCGGAGGCGGCTCTGGCGGAGGCGGCTCTGGCGGAGGCGGCAGCCAGATC

GTGCTGACCCAGAGCCCAGCCATCATGAGCGCCAGCCCAGGCGAGAAGGT

GACCATGACCTGCAGCGCCAGCAGCAGCGTGAGCTACATGAACTGGTACC

AGCAGAAGAGCGGCACCAGCCCCAAGCGGTGGATCTACGACACCAGCAAG

CTGGCCAGCGGCGTGCCAGCCCACTTCAGAGGCAGCGGCAGCGGCACCAG

CTACAGCCTGACCATCAGCGGCATGGAGGCCGAGGATGCCGCCACCTACT

ACTGCCAGCAGTGGAGCAGCAACCCCTTCACCTTCGGCAGCGGCACCAAG

CTGGAGATCAACCGGTCGTGA
```

The nucleic acid sequence may encode the same amino acid sequence as that encoded by SEQ ID No. 19, 20 or 21, but may have a different nucleic acid sequence, due to the degeneracy of the genetic code. The nucleic acid sequence may have at least 80, 85, 90, 95, 98 or 99% identity to the sequence shown as SEQ ID No. 19, 20 or 21, provided that it encodes a molecule as defined in the first aspect of the invention.

Vector

The present invention also provides a vector which comprises a nucleic acid sequence according to the present invention. Such a vector may be used to introduce the nucleic acid sequence into a host cell so that it expresses and produces a molecule according to the first aspect of the invention.

The vector may, for example, be a plasmid or a viral vector.

Host Cell

The invention also provides a host cell which comprises a nucleic acid according to the invention. The host cell may be capable of producing a molecule according to the first aspect of the invention.

The host cell may be a mammalian cell, such as the human embryonic kidney cell line 293.

The present invention also provides a method for producing a molecule according to the first aspect of the invention which comprises the step of culturing a host cell of the invention under conditions suitable for production of the molecule and then harvesting the molecule from the host cell or supernatant.

Bispecific molecules of the invention produced in a cell as set out above can be produced either intracellullarly (e.g. in the cytosol, in the periplasma or in inclusion bodies) and then isolated from the host cells and optionally further purified; or they can be produced extracellularly (e.g. in the medium in which the host cells are cultured) and then isolated from the culture medium and optionally further purified.

Pharmaceutical Composition

The present invention also relates to pharmaceutical compositions containing, as the active ingredient, at least one bispecific molecule of the invention together with a pharmaceutically acceptable carrier, diluent or excipient and/or adjuvant, and optionally one or more further pharmaceutically active polypeptides and/or compounds. Such a formulation may, for example, be in a form suitable for oral administration or for parenteral administration (such as by intravenous, intramuscular or subcutaneous injection or intravenous infusion).

Method of Treatment

The molecule of the present invention may be used for the treatment of a cancerous disease, in particular a plasma cell disorder or a B cell disorder which correlates with enhanced BCMA expression.

Plasma cell disorders include plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma (POEMS Syndrome) and heavy chain diseases as well as the clinically unclear monoclonal gammopathy of undetermined significance/smoldering multiple myeloma.

The disease may be multiple myeloma.

Examples for B cell disorders which correlate with elevated BCMA expression levels are CLL (chronic lymphocytic leukemia) and non-Hodgkins lymphoma (NHL). The bispecific binding agents of the invention may also be used in the therapy of autoimmune diseases like Systemic Lupus Erythematosus (SLE), multiple sclerosis (MS) and rheumatoid arthritis (RA).

The method of the present invention may be for treating a cancerous disease, in particular a plasma cell disorder or a B cell disorder which correlates with enhanced BCMA expression.

A method for the treatment of disease relates to the therapeutic use of the molecule of the invention. Herein the molecule may be administered to a subject having an existing disease or condition in order to lessen, reduce or improve at least one symptom associated with the disease and/or to slow down, reduce or block the progression of the disease. The molecule or pharmaceutical composition of the invention may cause or promote T-cell mediated killing of BCMA-expressing cells, such as plasma cells.

The invention will now be further described by way of Examples, which are meant to serve to assist one of ordinary skill in the art in carrying out the invention and are not intended in any way to limit the scope of the invention.

EXAMPLES

Example 1

Construction of a Series of "APRILITES"

The present inventors have constructed a series of bi-specific engagers which connect a scFv from OKT3 to the extracellular domain of APRIL, as shown in FIG. 2A. Several design considerations were made during the construction of these molecules: (a) the proteoglycan binding amino terminus of APRIL was truncated to prevent non-specific binding; (b) in constructs 4, 5 and 6, a signal peptide was attached to the mature ectodomain of APRIL; (c) the OKT3 was re-formatted as a scFv with a linker connecting the heavy and light chain variable regions; (d) various different spacers were tried between the scFv and APRIL.

The various different formats were as follows:
(1) OKT3 scFv connected to truncated APRIL by the IgG1 hinge;
(2) OKT3 scFv connected to truncated APRIL via a (SGGGGS)3 (SEQ ID No. 22 linker;
(3) OKT3 scFv connected to truncated APRIL via the CD8 stalk;

(4) truncated APRIL connected to OKT3 scFv via an IgG1 hinge;
(5) truncated APRIL connected to the OKT3 scFv via a (SGGGGS)3 (SEQ ID No. 22) linker; and
(6) truncated APRIL connected to the OKT3 scFv via a CD8 spacer.

Constructs (3) and (6) form homodimers through disulphide bonds in the CD8 spacer.

The amino acid sequences for constructs(1), (3) and (6) are shown in FIG. 8.

Example 2

Expression of APRILiTEs in 293T Cells

293 T cells were transfected with expression plasmids coding for the APRILiTE constructs listed above. Supernatant from the 293T cells was run on an acrylamide gel and proteins transferred to a membrane. The membrane was then stained with an antibody which recognized APRIL. The results are shown in FIG. 3. Proteins 1, 3 and 6 were detected at the expected molecular weight. Proteins 2, 4 and 5 were not detected, indicating that these configurations are unstable.

Example 3

Binding to TCR and BCMA

It was then investigated whether these proteins could bind either the T-cell receptor (TCR) on one end, and BCMA on the other end. Supernatant from 293T cells transfected was used to stain Jurkat T-cells and a Jurkat T-cell clone which has TCRαβ knocked out. This demonstrates the APRILiTE binds the TCR (FIG. 4b). SupT1 cells engineered to express BCMA and SupT1 cells engineered to express TACI were then stained with the above supernatant, using a secondary anti-APRIL biotin followed by streptavidin PE. The results are shown in FIG. 4a. It was found that APRILiTES 1,3 and 6 bound BCMA, and TACI to a lesser extent.

Example 4

Stable APRILITEs Trigger IFNγ Release

Normal donor T-cells were cultivated 1:1 with different SupT1 s. The SupT1s used were either non-transduced, engineered to express BCMA or engineered to express TACI. The results are shown in FIG. 5. It was found that T-cells only released IFNγ in the presence of either APRILiTE when exposed with SupT1-cells engineered with BCMA or TACI. The response to BCMA was greater than that with TACI.

Example 5

Stable APRILITEs Trigger T-Cell Mediated Killing of BCMA+ Targets

T-cells were cultured 1:1 with wild-type SupT1 cells, SupT1 cells expressing BCMA and SupT1 cells expressing TACI in the absence of or in the presence of APRILiTEs 1,3 and 6. The results are shown in FIG. 6. The remaining T-cells are shown as a proportion of SupT1 cells present in the condition with no APRILiTE added.

Example 6

Investigating BCMA Expression on Primary Myeloma Cells

Four different myeloma samples were stained with the rat anti-human BCMA mAb Vicky1. The results are shown in FIG. 7. In clinically and morphologically typical myelomas (panels 2 to 4) intermediate or dim staining is seen.

Example 7

Investigating the Effect of APRILiTEs on Primary Myeloma Cells

Left over material from a diagnostic bone-marrow aspirate from two patients with known multiple BCMA+ myeloma was used. A CD138 magnetic bead selection was performed to purify myeloma cells from the aspirate. These cells were rested in complete culture medium for 48 hours and staining for BCMA was performed to check that they were in fact BCMA positive. It was found that the myeloma cells express BCMA but at low levels (FIG. 9).

Next, normal donor peripheral mononuclear cells which had been stimulated using OKT3 and CD28.2 were CD56 depleted to remove NK cells. A 1:1 co-culture of CD56 depleted PBMCs and CD138 selected primary Myeloma cells were performed in the absence or presence of either APRILITE #03 and #06. Insufficient material was present to test APRILiTE #01. The co-cultures were observed by microscopy.

Interferon gamma release into supernatant was measured by ELISA. Survival of myeloma cells was measured by Annexin V/PI staining and bead-count controlled flow-cytometry.

Figure 10:
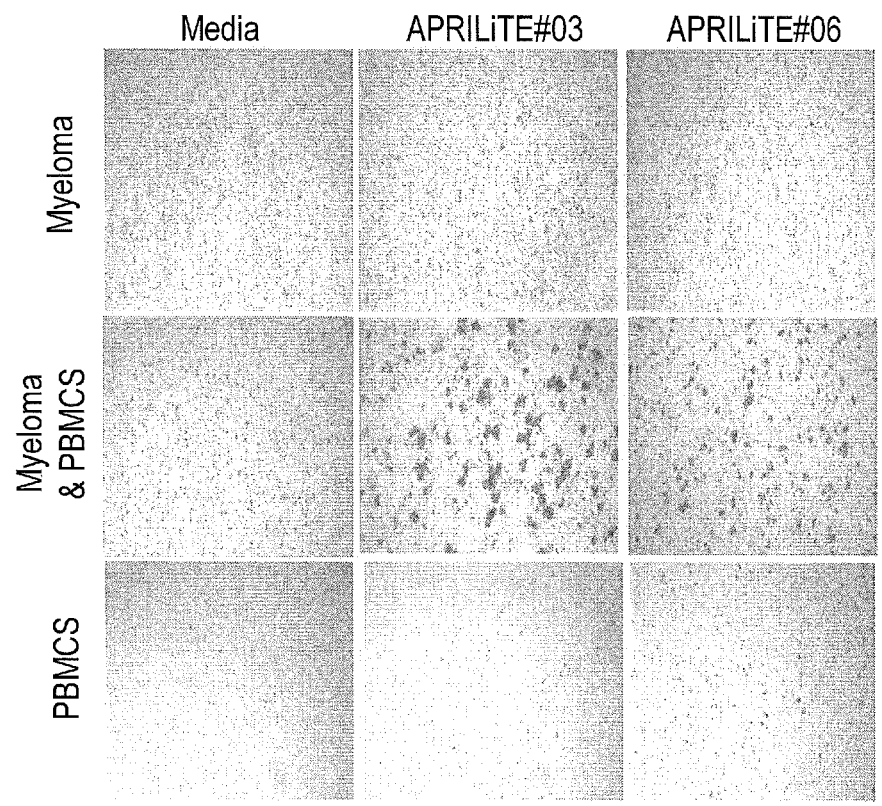

Clear clumping (a sign of T-cell activation) was seen upon co-culture (see FIG. 10).

Interferon-gamma release was observed in conditions where PBMCs were cultured with Myeloma cells in the presence of the APRILiTES, albeit at less absolute amounts than when co-cultured with SupT1. BCMA cells (FIG. 11). Killing of Myeloma cells was also observed when PBMCs were present with APRILiTE after 6 days of co-culture (FIG. 12).

These findings demonstrate that APRILiTEs cause T cell activation in the presence of primary myeloma cells at a level sufficient to cause T-cell mediated killing of the myeloma cells.

Example 8

Testing the APRILiTES in Vivo

A huSCID model is used: NSG (nod-scid gamma, NOD-scid IL2Rgamma$^{null}$) mice are xenografted with a myeloma cell line which expresses typical levels of BCMA. These lines are engineered to express firefly Luciferase to measure disease by bioluminescence imaging. Normal donor PBMCs are administered via the tail vein during concomitant intraperitoneal administration of APRILiTEs. The following are sequentially measured (1) serum levels of APRILiTEs; (2) serum levels of human Interferon-gamma; (3) peripheral blood T-cell expansion, engraftment and activation by flow cytometry; (4) Bioluminescence measurement of tumour. At take-down, the following are measured: (1) tumour burden by marrow histology; (2) T-cell proliferation and engraftment by flow cytometry of marrow, spleen, blood and lymph nodes; and (3) the remaining tissues are examined grossly and immunohistochemically for any toxicity.

All publications mentioned in the above specification are herein incorporated by reference. Various modifications and variations of the described methods and system of the invention will be apparent to those skilled in the art without departing from the scope and spirit of the invention.

Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. A bi-specific T-cell engager which comprises:
   (i) a first domain which comprises a truncated A proliferation-inducing ligand (APRIL)/TNF Superfamily Member 13 Protein (TNFSF13), which comprises the BCMA binding site of APRIL, wherein truncated APRIL comprises the sequence shown as SEQ ID No. 2 or a sequence which has at least 90% sequence identity to SEQ ID No. 2 and binds BCMA; and
   (ii) a second domain which comprises a CD3-specific antibody or an antigen binding fragment thereof comprising complementarity determining regions (CDRs) from an scFv sequence shown as SEQ ID No. 9;
   wherein said first domain and said second domain are connected by a spacer.

2. A bi-specific T-cell engager according to claim 1, wherein the second domain comprises the scFv sequence shown as SEQ ID No. 9 or a sequence which has at least 90% sequence identity to SEQ ID No. 9 and comprises the complementarity determining regions (CDRs) from SEQ ID No. 9 and binds CD3.

3. A bi-specific T-cell engager according to claim 1, wherein the spacer comprises an IgG1 hinge or a CD8 stalk.

4. A bi-specific T-cell engager according to claim 1, which comprises the sequence shown as SEQ ID No. 10, 11 or 12 or a sequence which has at least 90% sequence identity to SEQ ID No. 10, 11 or 12 and comprises the CDRs from the sequence of SEQ ID No. 10, 11 or 12, and wherein the bispecific T-cell engager i) binds BCMA and ii) activates a T cell.

5. A bi-specific T-cell engager according to claim 1, which binds to BCMA in a three-fold subunit cluster.

6. A pharmaceutical composition which comprises a bi-specific T-cell engager according to claim 1, together with a pharmaceutically acceptable carrier, diluent or excipient.

7. A nucleic acid sequence which encodes a bi-specific T-cell engager according to claim 1.

8. A nucleic acid sequence according to claim 7 which comprises the sequence shown as SEQ ID No 19, 20 or 21 or a variant thereof having at least 80% sequence identity to SEQ ID No 19, 20 or 21 and which encodes the CDRs from the sequence of SEQ ID No. 10, 11 or 12, and wherein the encoded bispecific T-cell engager i) binds BCMA and ii) activates a T cell.

9. A vector which comprises a nucleic acid sequence according to claim 7.

10. A host cell which comprises a nucleic acid sequence according to claim 7 and expresses a bi-specific T-cell engager.

11. A method for producing a bi-specific T-cell engager which comprises the step of culturing a host cell of claim 10 under conditions such that the bi-specific T-cell engager is produced.

* * * * *

UNITED STATES PATENT AND TRADEMARK OFFICE
CERTIFICATE OF CORRECTION

PATENT NO. : 11,492,408 B2
APPLICATION NO. : 15/028113
DATED : November 8, 2022
INVENTOR(S) : Martin Pulé et al.

Page 1 of 1

It is certified that error appears in the above-identified patent and that said Letters Patent is hereby corrected as shown below:

In the Claims

At Column 37, Line 44, "Protein (TNFSF13)," should be -- (TNFSF13) Protein, --.

At Column 38, Line 41, "bispecific T-cell engager i) binds BCMA and ii)" should be -- bi-specific T-cell engager (i) binds BCMA and (ii) --.

At Column 38, Line 51, "No" should be -- No. --.

At Column 38, Line 53, "No" should be -- No. --.

At Column 38, Line 55, "bispecific T-cell engager i) binds BCMA and ii)" should be -- bi-specific T-cell engager (i) binds BCMA and (ii) --.

Signed and Sealed this
Thirteenth Day of June, 2023

Katherine Kelly Vidal
*Director of the United States Patent and Trademark Office*

SEQUENCE LISTING

```
<160> NUMBER OF SEQ ID NOS: 24

<210> SEQ ID NO 1
<211> LENGTH: 250
<212> TYPE: PRT
<213> ORGANISM: Homo sapiens

<400> SEQUENCE: 1

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 2
<211> LENGTH: 134
<212> TYPE: PRT
<213> ORGANISM: Homo sapiens

<400> SEQUENCE: 2

Val Leu His Leu Val Pro Ile Asn Ala Thr Ser Lys Asp Ser Asp
1               5                   10                  15
```

```
Val Thr Glu Val Met Trp Gln Pro Ala Leu Arg Arg Gly Arg Gly Leu
             20                  25                  30

Gln Ala Gln Gly Tyr Gly Val Arg Ile Gln Asp Ala Gly Val Tyr Leu
         35                  40                  45

Leu Tyr Ser Gln Val Leu Phe Gln Asp Val Thr Phe Thr Met Gly Gln
     50                  55                  60

Val Val Ser Arg Glu Gly Gln Gly Arg Gln Glu Thr Leu Phe Arg Cys
 65                  70                  75                  80

Ile Arg Ser Met Pro Ser His Pro Asp Arg Ala Tyr Asn Ser Cys Tyr
                 85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130
```

```
<210> SEQ ID NO 3
<211> LENGTH: 13
<212> TYPE: PRT
<213> ORGANISM: Artificial Sequence
<220> FEATURE:
<223> OTHER INFORMATION: Heavy chain CDR1

<400> SEQUENCE: 3

Lys Ala Ser Gly Tyr Thr Phe Thr Arg Tyr Thr Met His
1               5                   10
```

```
<210> SEQ ID NO 4
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 4

Ile Asn Pro Ser Arg Gly Tyr Thr Asn Tyr Asn Gln Lys Phe Lys Asp
1               5                   10                  15
```

```
<210> SEQ ID NO 5
<211> LENGTH: 10
<212> TYPE: PRT
<213> ORGANISM: Artificial Sequence
<220> FEATURE:
<223> OTHER INFORMATION: Heavy chain CDR3

<400> SEQUENCE: 5

Tyr Tyr Asp Asp His Tyr Cys Leu Asp Tyr
1               5                   10
```

```
<210> SEQ ID NO 6
<211> LENGTH: 10
<212> TYPE: PRT
<213> ORGANISM: Artificial Sequence
<220> FEATURE:
<223> OTHER INFORMATION: Light chain CDR1

<400> SEQUENCE: 6

Ser Ala Ser Ser Ser Val Ser Tyr Met Asn
1               5                   10
```

<210> SEQ ID NO 7
<211> LENGTH: 11
<212> TYPE: PRT
<213> ORGANISM: Artificial Sequence
<220> FEATURE:
<223> OTHER INFORMATION: Light chain CDR2

<400> SEQUENCE: 7

Arg Trp Ile Tyr Asp Thr Ser Lys Leu Ala Ser
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Light chain CDR3

<400> SEQUENCE: 8

Gln Gln Trp Ser Ser Asn Pro Phe Thr
1               5

<210> SEQ ID NO 9
<211> LENGTH: 242
<212> TYPE: PRT
<213> ORGANISM: Artificial Sequence
<220> FEATURE:
<223> OTHER INFORMATION: scFv sequence

<400> SEQUENCE: 9

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Gly Ser Gly Gly Gly Gly Ser Gln Ile Val Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Val Ser Tyr Met Asn Trp Tyr Gln Gln Lys Ser Gly Thr
                165                 170                 175

Ser Pro Lys Arg Trp Ile Tyr Asp Thr Ser Lys Leu Ala Ser Gly Val
            180                 185                 190

Pro Ala His Phe Arg Gly Ser Gly Ser Gly Thr Ser Tyr Ser Leu Thr
        195                 200                 205

Ile Ser Gly Met Glu Ala Glu Asp Ala Ala Thr Tyr Tyr Cys Gln Gln
    210                 215                 220

```
Trp Ser Ser Asn Pro Phe Thr Phe Gly Ser Gly Thr Lys Leu Glu Ile
225                 230                 235                 240

Asn Arg

<210> SEQ ID NO 10
<211> LENGTH: 425
<212> TYPE: PRT
<213> ORGANISM: Artificial Sequence
<220> FEATURE:
<223> OTHER INFORMATION: Sequence of bi-specific molecule

<400> SEQUENCE: 10

Met Glu Thr Asp Thr Leu Leu Leu Trp Val Leu Leu Leu Trp Val Pro
1               5                   10                  15

Gly Ser Thr Gly Gln Val Gln Leu Gln Gln Ser Gly Ala Glu Leu Ala
            20                  25                  30

Arg Pro Gly Ala Ser Val Lys Met Ser Cys Lys Ala Ser Gly Tyr Thr
        35                  40                  45

Phe Thr Arg Tyr Thr Met His Trp Val Lys Gln Arg Pro Gly Gln Gly
    50                  55                  60

Leu Glu Trp Ile Gly Tyr Ile Asn Pro Ser Arg Gly Tyr Thr Asn Tyr
65                  70                  75                  80

Asn Gln Lys Phe Lys Asp Lys Ala Thr Leu Thr Thr Asp Lys Ser Ser
                85                  90                  95

Ser Thr Ala Tyr Met Gln Leu Ser Ser Leu Thr Ser Glu Asp Ser Ala
            100                 105                 110

Val Tyr Tyr Cys Ala Arg Tyr Tyr Asp Asp His Tyr Cys Leu Asp Tyr
        115                 120                 125

Trp Gly Gln Gly Thr Thr Leu Thr Val Ser Ser Gly Gly Gly Gly
130                 135                 140

Ser Gly Gly Gly Gly Ser Gly Gly Gly Gly Ser Gln Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Val Ser Tyr Met Asn Trp Tyr Gln Gln
            180                 185                 190

Lys Ser Gly Thr Ser Pro Lys Arg Trp Ile Tyr Asp Thr Ser Lys Leu
        195                 200                 205

Ala Ser Gly Val Pro Ala His Phe Arg Gly Ser Gly Ser Gly Thr Ser
    210                 215                 220

Tyr Ser Leu Thr Ile Ser Gly Met Glu Ala Glu Asp Ala Ala Thr Tyr
225                 230                 235                 240

Tyr Cys Gln Gln Trp Ser Ser Asn Pro Phe Thr Phe Gly Ser Gly Thr
                245                 250                 255

Lys Leu Glu Ile Asn Arg Ser Asp Pro Ala Glu Pro Lys Ser Pro Asp
            260                 265                 270

Lys Thr His Thr Cys Pro Pro Cys Pro Lys Asp Pro Lys Ser Gly Gly
        275                 280                 285

Gly Gly Ser Val Leu His Leu Val Pro Ile Asn Ala Thr Ser Lys Asp
    290                 295                 300

Asp Ser Asp Val Thr Glu Val Met Trp Gln Pro Ala Leu Arg Arg Gly
305                 310                 315                 320

Arg Gly Leu Gln Ala Gln Gly Tyr Gly Val Arg Ile Gln Asp Ala Gly
                325                 330                 335
```

Val Tyr Leu Leu Tyr Ser Gln Val Leu Phe Gln Asp Val Thr Phe Thr
             340                 345                 350

Met Gly Gln Val Val Ser Arg Glu Gly Gln Gly Arg Gln Glu Thr Leu
             355                 360                 365

Phe Arg Cys Ile Arg Ser Met Pro Ser His Pro Asp Arg Ala Tyr Asn
370                 375                 380

Ser Cys Tyr Ser Ala Gly Val Phe His Leu His Gln Gly Asp Ile Leu
385                 390                 395                 400

Ser Val Ile Ile Pro Arg Ala Arg Ala Lys Leu Asn Leu Ser Pro His
                 405                 410                 415

Gly Thr Phe Leu Gly Phe Val Lys Leu
             420                 425

<210> SEQ ID NO 11
<211> LENGTH: 450
<212> TYPE: PRT
<213> ORGANISM: Artificial Sequence
<220> FEATURE:
<223> OTHER INFORMATION: Sequence of bi-specific molecule

<400> SEQUENCE: 11

Met Glu Thr Asp Thr Leu Leu Leu Trp Val Leu Leu Leu Trp Val Pro
1               5                   10                  15

Gly Ser Thr Gly Gln Val Gln Leu Gln Gln Ser Gly Ala Glu Leu Ala
             20                  25                  30

Arg Pro Gly Ala Ser Val Lys Met Ser Cys Lys Ala Ser Gly Tyr Thr
         35                  40                  45

Phe Thr Arg Tyr Thr Met His Trp Val Lys Gln Arg Pro Gly Gln Gly
     50                  55                  60

Leu Glu Trp Ile Gly Tyr Ile Asn Pro Ser Arg Gly Tyr Thr Asn Tyr
65                  70                  75                  80

Asn Gln Lys Phe Lys Asp Lys Ala Thr Leu Thr Thr Asp Lys Ser Ser
                 85                  90                  95

Ser Thr Ala Tyr Met Gln Leu Ser Ser Leu Thr Ser Glu Asp Ser Ala
             100                 105                 110

Val Tyr Tyr Cys Ala Arg Tyr Tyr Asp Asp His Tyr Cys Leu Asp Tyr
         115                 120                 125

Trp Gly Gln Gly Thr Thr Leu Thr Val Ser Ser Ser Gly Gly Gly Gly
     130                 135                 140

Ser Gly Gly Gly Gly Ser Gly Gly Gly Gly Ser Gln Ile Val Leu Thr
145                 150                 155                 160

Gln Ser Pro Ala Ile Met Ser Ala Ser Pro Gly Glu Lys Val Thr Met
                 165                 170                 175

Thr Cys Ser Ala Ser Ser Ser Val Ser Tyr Met Asn Trp Tyr Gln Gln
             180                 185                 190

Lys Ser Gly Thr Ser Pro Lys Arg Trp Ile Tyr Asp Thr Ser Lys Leu
         195                 200                 205

Ala Ser Gly Val Pro Ala His Phe Arg Gly Ser Gly Ser Gly Thr Ser
     210                 215                 220

Tyr Ser Leu Thr Ile Ser Gly Met Glu Ala Glu Asp Ala Ala Thr Tyr
225                 230                 235                 240

Tyr Cys Gln Gln Trp Ser Ser Asn Pro Phe Thr Phe Gly Ser Gly Thr
                 245                 250                 255

Lys Leu Glu Ile Asn Arg Ser Asp Pro Thr Thr Thr Pro Ala Pro Arg
             260                 265                 270

```
Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
        290                 295                 300

Leu Asp Phe Ala Cys Asp Ser Gly Gly Gly Ser Val Leu His Leu
305                 310                 315                 320

Val Pro Ile Asn Ala Thr Ser Lys Asp Asp Ser Asp Val Thr Glu Val
                325                 330                 335

Met Trp Gln Pro Ala Leu Arg Arg Gly Arg Gly Leu Gln Ala Gln Gly
                340                 345                 350

Tyr Gly Val Arg Ile Gln Asp Ala Gly Val Tyr Leu Leu Tyr Ser Gln
                355                 360                 365

Val Leu Phe Gln Asp Val Thr Phe Thr Met Gly Gln Val Val Ser Arg
370                 375                 380

Glu Gly Gln Gly Arg Gln Glu Thr Leu Phe Arg Cys Ile Arg Ser Met
385                 390                 395                 400

Pro Ser His Pro Asp Arg Ala Tyr Asn Ser Cys Tyr Ser Ala Gly Val
                405                 410                 415

Phe His Leu His Gln Gly Asp Ile Leu Ser Val Ile Ile Pro Arg Ala
                420                 425                 430

Arg Ala Lys Leu Asn Leu Ser Pro His Gly Thr Phe Leu Gly Phe Val
                435                 440                 445

Lys Leu
    450

<210> SEQ ID NO 12
<211> LENGTH: 456
<212> TYPE: PRT
<213> ORGANISM: Artificial Sequence
<220> FEATURE:
<223> OTHER INFORMATION: Sequence of bi-specific molecule

<400> SEQUENCE: 12

Met Gly Thr Ser Leu Leu Cys Trp Met Ala Leu Cys Leu Leu Gly Ala
1               5                   10                  15

Asp His Ala Asp Gly Val Leu His Leu Val Pro Ile Asn Ala Thr Ser
                20                  25                  30

Lys Asp Asp Ser Asp Val Thr Glu Val Met Trp Gln Pro Ala Leu Arg
            35                  40                  45

Arg Gly Arg Gly Leu Gln Ala Gln Gly Tyr Gly Val Arg Ile Gln Asp
        50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
130                 135                 140

Pro His Gly Thr Phe Leu Gly Phe Val Lys Leu Ser Gly Gly Gly Ser
145                 150                 155                 160

Asp Pro Thr Thr Thr Pro Ala Pro Arg Pro Pro Thr Pro Ala Pro Thr
                165                 170                 175
```

```
Ile Ala Ser Gln Pro Leu Ser Leu Arg Pro Glu Ala Cys Arg Pro Ala
                180                 185                 190

Ala Gly Gly Ala Val His Thr Arg Gly Leu Asp Phe Ala Cys Asp Ser
            195                 200                 205

Gly Gly Gly Gly Ser Gln Val Gln Leu Gln Gln Ser Gly Ala Glu Leu
        210                 215                 220

Ala Arg Pro Gly Ala Ser Val Lys Met Ser Cys Lys Ala Ser Gly Tyr
225                 230                 235                 240

Thr Phe Thr Arg Tyr Thr Met His Trp Val Lys Gln Arg Pro Gly Gln
                245                 250                 255

Gly Leu Glu Trp Ile Gly Tyr Ile Asn Pro Ser Arg Gly Tyr Thr Asn
            260                 265                 270

Tyr Asn Gln Lys Phe Lys Asp Lys Ala Thr Leu Thr Thr Asp Lys Ser
        275                 280                 285

Ser Ser Thr Ala Tyr Met Gln Leu Ser Ser Leu Thr Ser Glu Asp Ser
    290                 295                 300

Ala Val Tyr Tyr Cys Ala Arg Tyr Tyr Asp Asp His Tyr Cys Leu Asp
305                 310                 315                 320

Tyr Trp Gly Gln Gly Thr Thr Leu Thr Val Ser Ser Gly Gly Gly
                325                 330                 335

Gly Ser Gly Gly Gly Gly Ser Gly Gly Gly Gly Ser Gln Ile Val Leu
            340                 345                 350

Thr Gln Ser Pro Ala Ile Met Ser Ala Ser Pro Gly Glu Lys Val Thr
        355                 360                 365

Met Thr Cys Ser Ala Ser Ser Ser Val Ser Tyr Met Asn Trp Tyr Gln
    370                 375                 380

Gln Lys Ser Gly Thr Ser Pro Lys Arg Trp Ile Tyr Asp Thr Ser Lys
385                 390                 395                 400

Leu Ala Ser Gly Val Pro Ala His Phe Arg Gly Ser Gly Ser Gly Thr
                405                 410                 415

Ser Tyr Ser Leu Thr Ile Ser Gly Met Glu Ala Glu Asp Ala Ala Thr
            420                 425                 430

Tyr Tyr Cys Gln Gln Trp Ser Ser Asn Pro Phe Thr Phe Gly Ser Gly
        435                 440                 445

Thr Lys Leu Glu Ile Asn Arg Ser
    450                 455

<210> SEQ ID NO 13
<211> LENGTH: 20
<212> TYPE: PRT
<213> ORGANISM: Artificial Sequence
<220> FEATURE:
<223> OTHER INFORMATION: Signal peptide

<400> SEQUENCE: 13

Met Glu Thr Asp Thr Leu Leu Leu Trp Val Leu Leu Leu Trp Val Pro
1               5                   10                  15

Gly Ser Thr Gly
            20

<210> SEQ ID NO 14
<211> LENGTH: 21
<212> TYPE: PRT
<213> ORGANISM: Artificial Sequence
<220> FEATURE:
<223> OTHER INFORMATION: Signal peptide
```

```
<400> SEQUENCE: 14

Met Gly Thr Ser Leu Leu Cys Trp Met Ala Leu Cys Leu Leu Gly Ala
1               5                   10                  15

Asp His Ala Asp Gly
            20

<210> SEQ ID NO 15
<211> LENGTH: 26
<212> TYPE: PRT
<213> ORGANISM: Artificial Sequence
<220> FEATURE:
<223> OTHER INFORMATION: Spacer sequence (IgG1 hinge)

<400> SEQUENCE: 15

Ala Glu Pro Lys Ser Pro Asp Lys Thr His Thr Cys Pro Pro Cys Pro
1               5                   10                  15

Lys Asp Pro Lys Ser Gly Gly Gly Gly Ser
            20                  25

<210> SEQ ID NO 16
<211> LENGTH: 45
<212> TYPE: PRT
<213> ORGANISM: Artificial Sequence
<220> FEATURE:
<223> OTHER INFORMATION: Spacer sequence (CD8 stalk)

<400> SEQUENCE: 16

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 17
<211> LENGTH: 7
<212> TYPE: PRT
<213> ORGANISM: Artificial Sequence
<220> FEATURE:
<223> OTHER INFORMATION: Chain break linker motif

<400> SEQUENCE: 17

Ser Gly Gly Gly Ser Asp Pro
1               5

<210> SEQ ID NO 18
<211> LENGTH: 6
<212> TYPE: PRT
<213> ORGANISM: Artificial Sequence
<220> FEATURE:
<223> OTHER INFORMATION: Serine-glycine linker

<400> SEQUENCE: 18

Ser Gly Gly Gly Gly Ser
1               5

<210> SEQ ID NO 19
<211> LENGTH: 1278
<212> TYPE: DNA
<213> ORGANISM: Artificial Sequence
<220> FEATURE:
<223> OTHER INFORMATION: Nucleic acid sequence coding for a bi-specific
      molecule
```

<400> SEQUENCE: 19

```
atggagaccg acaccctgct gctgtgggtg ctgctgctgt gggtgccagg cagcaccggc      60
caggtgcagc tgcagcagag cggagccgag ctggccagac aggcgccag cgtgaagatg      120
agctgcaagg ccagcggcta caccttcacc cggtacacca tgcactgggt gaagcagcgg      180
ccaggccagg gcctggagtg gatcggctac atcaaccca gcagaggcta caccaactac      240
aaccagaagt tcaaggacaa ggccaccctg accaccgaca gagcagcag caccgcctac      300
atgcagctga gcagcctgac cagcgaggac agcgccgtgt actactgcgc cagatactac      360
gacgaccact actgcctgga ctactggggc cagggcacca ccctgaccgt gagcagctct      420
ggcggaggcg gctctggcgg aggcggctct ggcggaggcg gcagccagat cgtgctgacc      480
cagagcccag ccatcatgag cgccagccca ggcgagaagg tgaccatgac ctgcagcgcc      540
agcagcagcg tgagctacat gaactggtac cagcagaaga gcggcaccag ccccaagcgg      600
tggatctacg acaccagcaa gctggccagc ggcgtgccag cccacttcag aggcagcggc      660
agcggcacca gctacagcct gaccatcagc ggcatggagg ccgaggatgc cgccacctac      720
tactgccagc agtggagcag caaccccttc accttcggca gcggcaccaa gctggagatc      780
aaccggtcgg atcccgccga gcccaaatct cctgacaaaa ctcacacatg cccaccgtgc      840
ccaaaagatc ccaaatctgg cggaggcggc agcgtgctgc acctggtgcc catcaacgcc      900
accagcaagg acgactctga tgtgaccgag gtgatgtggc agccagccct gagacggggc      960
agaggcctgc aggcccaggg ctacggcgtg agaatccagg acgctggcgt gtacctgctg      1020
tactcccagg tgctgttcca ggacgtgacc ttcacaatgg ccaggtggt gagccgggag      1080
ggccagggca gacaggagac cctgttccgg tgcatccgga gcatgccag ccaccccgac      1140
agagcctaca cagctgcta cagcgctggc gtgtttcacc tgcaccaggg cgacatcctg      1200
agcgtgatca tccccagagc cagagccaag ctgaacctgt cccccacgg caccttctg      1260
ggcttcgtga agctgtga                                                    1278
```

<210> SEQ ID NO 20
<211> LENGTH: 1353
<212> TYPE: DNA
<213> ORGANISM: Artificial Sequence
<220> FEATURE:
<223> OTHER INFORMATION: Nucleic acid sequence coding for a bi-specific molecule

<400> SEQUENCE: 20

```
atggagaccg acaccctgct gctgtgggtg ctgctgctgt gggtgccagg cagcaccggc      60
caggtgcagc tgcagcagag cggagccgag ctggccagac aggcgccag cgtgaagatg      120
agctgcaagg ccagcggcta caccttcacc cggtacacca tgcactgggt gaagcagcgg      180
ccaggccagg gcctggagtg gatcggctac atcaaccca gcagaggcta caccaactac      240
aaccagaagt tcaaggacaa ggccaccctg accaccgaca gagcagcag caccgcctac      300
atgcagctga gcagcctgac cagcgaggac agcgccgtgt actactgcgc cagatactac      360
gacgaccact actgcctgga ctactggggc cagggcacca ccctgaccgt gagcagctct      420
ggcggaggcg gctctggcgg aggcggctct ggcggaggcg gcagccagat cgtgctgacc      480
cagagcccag ccatcatgag cgccagccca ggcgagaagg tgaccatgac ctgcagcgcc      540
agcagcagcg tgagctacat gaactggtac cagcagaaga gcggcaccag ccccaagcgg      600
tggatctacg acaccagcaa gctggccagc ggcgtgccag cccacttcag aggcagcggc      660
```

```
agcggcacca gctacagcct gaccatcagc ggcatggagg ccgaggatgc cgccacctac      720
tactgccagc agtggagcag caacccttc accttcggca gcggcaccaa gctggagatc      780
aaccggtcgg atcccaccac gacgccagcg ccgcgaccac caacaccggc gcccaccatc      840
gcgtcgcagc ccctgtccct gcgcccagag gcgtgccggc cagcggcggg gggcgcagtg      900
cacacgaggg ggctggactt cgcctgtgat tctggcggag cggcagcgt gctgcacctg       960 gtgcccatca cgccaccag caaggacgac tctgatgtga ccgaggtgat gtggcagcca       1020
gccctgagac ggggcagagg cctgcaggcc cagggctacg gcgtgagaat ccaggacgct      1080
ggcgtgtacc tgctgtactc ccaggtgctg ttccaggacg tgaccttcac aatgggccag      1140
gtggtgagcc gggagggcca gggcagacag agaccctgt tccggtgcat ccggagcatg       1200
cccagccacc ccgacagagc ctacaacagc tgctacagcg ctggcgtgtt tcacctgcac      1260
cagggcgaca tcctgagcgt gatcatcccc agagccagag ccaagctgaa cctgtccccc     1320
cacggcacct ttctgggctt cgtgaagctg tga                                  1353

<210> SEQ ID NO 21
<211> LENGTH: 1371
<212> TYPE: DNA
<213> ORGANISM: Artificial Sequence
<220> FEATURE:
<223> OTHER INFORMATION: Nucleic acid sequence coding for a bi-specific
      molecule

<400> SEQUENCE: 21
atgggcacct ccctgctgtg ctggatggcc ctgtgcctgc tgggagccga ccacgccgac       60
ggcgtgctgc acctggtgcc catcaacgcc accagcaagg acgactctga tgtgaccgag      120
gtgatgtggc agccagccct gagacggggc agaggcctgc aggcccaggg ctacggcgtg      180
agaatccagg acgctggcgt gtacctgctg tactcccagg tgctgttcca ggacgtgacc      240
ttcacaatgg gccaggtggt gagccgggag ggccagggca gacaggagac cctgttccgg      300
tgcatccgga gcatgcccag ccaccccgac agagcctaca acagctgcta cagcgctggc      360
gtgtttcacc tgcaccaggg cgacatcctg agcgtgatca tccccagagc cagagccaag      420
ctgaacctgt cccccacgg caccttttctg gcttcgtga agctgtctgg aggcggctcg       480
gatcccacca cgacgccagc gccgcgacca ccaacaccgg cgcccaccat cgcgtcgcag      540
cccctgtccc tgcgcccaga ggcgtgccgg ccagcggcgg ggggcgcagt gcacacgagg      600
gggctggact cgcctgtgat agcggtggc ggtggcagcc aggtgcagct gcagcagagc       660
ggagccgagc tggccagacc aggcgccagc gtgaagatga gctgcaaggc cagcggctac      720
accttcaccc ggtacaccat gcactgggtg aagcagcggc caggccaggg cctggagtgg      780
atcggctaca tcaaccccag cagaggctac accaactaca accagaagtt caaggacaag      840
gccaccctga ccaccgacaa gagcagcagc accgcctaca tgcagctgag cagcctgacc      900
agcgaggaca gcgccgtgta ctactgcgcc agatactacg acgaccacta ctgcctggac      960
tactggggcc agggcaccac cctgaccgtg agcagctctg gcgaggcgg ctctggcgga      1020 ggcggctctg gcggaggcgg cagccagatc gtgctgaccc agagcccagc catcatgagc     1080
gccagcccag gcgagaaggt gaccatgacc tgcagcgcca gcagcagcgt gagctacatg     1140
aactggtacc agcagaagag cggcaccagc cccaagcgt ggatctacga caccagcaag      1200 ctgccagcg gcgtgccagc ccacttcaga ggcagcggca gcggcaccag ctacagcctg     1260
```

```
accatcagcg gcatggaggc cgaggatgcc gccacctact actgccagca gtggagcagc    1320
aaccccttca ccttcggcag cggcaccaag ctggagatca accggtcgtg a             1371
```

<210> SEQ ID NO 22
<211> LENGTH: 18
<212> TYPE: PRT
<213> ORGANISM: Artificial Sequence
<220> FEATURE:
<223> OTHER INFORMATION: Linker

<400> SEQUENCE: 22

Ser Gly Gly Gly Gly Ser Ser Gly Gly Gly Gly Ser Ser Gly Gly Gly
1               5                   10                  15

Gly Ser

<210> SEQ ID NO 23
<211> LENGTH: 6
<212> TYPE: PRT
<213> ORGANISM: Homo sapiens

<400> SEQUENCE: 23

Lys Gln Lys Lys Gln Lys
1               5

<210> SEQ ID NO 24
<211> LENGTH: 5
<212> TYPE: PRT
<213> ORGANISM: Artificial Sequence
<220> FEATURE:
<223> OTHER INFORMATION: Linker

<400> SEQUENCE: 24

Gly Gly Gly Gly Ser
1               5